(12) United States Patent
Goodrich

(10) Patent No.: US 11,934,575 B2
(45) Date of Patent: *Mar. 19, 2024

(54) DETERMINING GAZE DIRECTION TO GENERATE AUGMENTED REALITY CONTENT

(71) Applicant: Snap Inc., Santa Monica, CA (US)

(72) Inventor: Kyle Goodrich, Venice, CA (US)

(73) Assignee: Snap Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/183,782

(22) Filed: Mar. 14, 2023

(65) Prior Publication Data

US 2023/0214013 A1 Jul. 6, 2023

Related U.S. Application Data

(63) Continuation of application No. 17/563,707, filed on Dec. 28, 2021, now Pat. No. 11,630,511.
(Continued)

(51) Int. Cl.
*G06F 3/01* (2006.01)
*G02B 27/00* (2006.01)
(Continued)

(52) U.S. Cl.
CPC ......... *G06F 3/013* (2013.01); *G02B 27/0093* (2013.01); *G02B 27/017* (2013.01);
(Continued)

(58) Field of Classification Search
CPC .............. G02B 27/0093; G02B 27/017; G02B 27/0179; G02B 2027/0178;
(Continued)

(56) References Cited

U.S. PATENT DOCUMENTS 10,902,628 B1  1/2021  Kharboutly et al.
11,630,511 B2  4/2023  Goodrich
(Continued)

FOREIGN PATENT DOCUMENTS

CN  116685935 A  9/2023
WO  WO-2022147031 A1  7/2022

OTHER PUBLICATIONS

"U.S. Appl. No. 17/563,707, Non Final Office Action dated Aug. 29, 2022", 13 pgs.
(Continued)

*Primary Examiner* — Nelson M Rosario
(74) *Attorney, Agent, or Firm* — Schwegman Lundberg & Woessner, P.A.

(57) ABSTRACT

The subject technology determines a gaze direction in a field of view of a user using an eyewear device. The subject technology generates an anchor point in the field of view based at least in part on the determined gaze direction. The subject technology identifies a surface corresponding to a ground plane in the field of view. The subject technology determines a distance from the identified surface to the anchor point. The subject technology generates AR content based at least in part on the determined distance. The subject technology renders the generated AR content in the field of view for display by the eyewear device.

20 Claims, 12 Drawing Sheets

Related U.S. Application Data

(60) Provisional application No. 63/133,143, filed on Dec. 31, 2020.

(51) Int. Cl.
- *G02B 27/01* (2006.01)
- *G06T 15/06* (2011.01)
- *G06T 19/00* (2011.01)
- *G06V 20/20* (2022.01)
- *G06V 40/19* (2022.01)

(52) U.S. Cl.
CPC .......... *G02B 27/0179* (2013.01); *G06T 15/06* (2013.01); *G06T 19/006* (2013.01); *G06V 20/20* (2022.01); *G06V 40/19* (2022.01); *G02B 2027/0178* (2013.01); *G02B 2027/0185* (2013.01); *G02B 2027/0187* (2013.01)

(58) Field of Classification Search
CPC .... G02B 2027/0185; G02B 2027/0187; G06F 3/013; G06T 15/06; G06T 19/006; G06V 20/20; G06V 40/19
See application file for complete search history.

(56) References Cited

U.S. PATENT DOCUMENTS

| | | |
|---|---|---|
| 2014/0333666 A1 | 11/2014 | Poulos et al. |
| 2020/0159318 A1 | 5/2020 | Kondo et al. |
| 2020/0279392 A1* | 9/2020 | Shamir ................ G06F 3/0304 |
| 2022/0206572 A1 | 6/2022 | Goodrich |

OTHER PUBLICATIONS

"U.S. Appl. No. 17/563,707, Notice of Allowance dated Dec. 14, 2022", 8 pgs.

"U.S. Appl. No. 17/563,707, Response filed Nov. 29, 2022 to Non Final Office Action dated Aug. 29, 2022", 9 pgs.

"International Application Serial No. PCT/US2021/065369, International Search Report dated Mar. 25, 2022", 4 pgs.

"International Application Serial No. PCT/US2021/065369, Written Opinion dated Mar. 25, 2022", 7 pgs.

"International Application Serial No. PCT/US2021/065369, International Preliminary Report on Patentability dated Jul. 13, 2023", 9 pgs.

* cited by examiner

DETERMINING GAZE DIRECTION TO GENERATE AUGMENTED REALITY CONTENT

PRIORITY CLAIM

This application is a continuation of U.S. patent application Ser. No. 17/563,707, filed Dec. 28, 2021, which application claims the benefit of priority of U.S. Provisional Patent Application No. 63/133,143, filed Dec. 31, 2020, which are hereby incorporated by reference herein in their entirety for all purposes.

BACKGROUND

With the increased use of digital images, affordability of portable computing devices, availability of increased capacity of digital storage media, and increased bandwidth and accessibility of network connections, digital images have become a part of the daily life for an increasing number of people.

Some electronics-enabled eyewear devices, such as so-called smart glasses, allow users to interact with virtual content while a user is engaged in some activity. Users wear the eyewear devices and can view a real-world environment through the eyewear devices while interacting with virtual content that is displayed by the eyewear devices.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
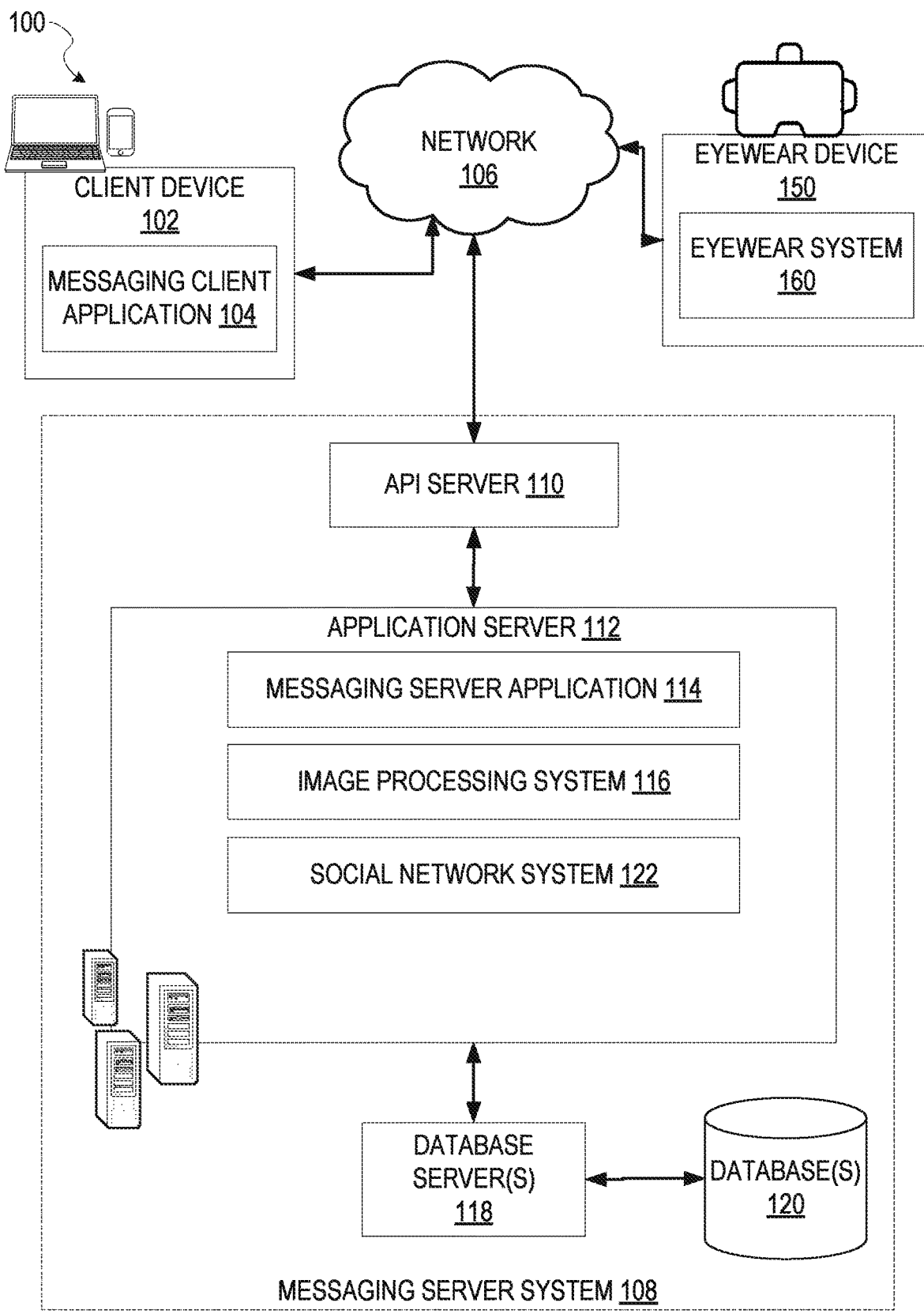
FIG. 1 is a diagrammatic representation of a networked environment in which the present disclosure may be deployed, in accordance with some example embodiments.

Users with a range of interests from various locations can capture digital images of various subjects and make captured images available to others via networks, such as the Internet. To enhance users' experiences with digital images and provide various features, enabling computing devices to perform image processing operations on various objects and/or features captured in a wide range of changing conditions (e.g., changes in image scales, noises, lighting, movement, or geometric distortion) can be challenging and computationally intensive.

Augmented reality technology aims to bridge a gap between virtual environments and a real world environment by providing an enhanced real world environment that is augmented with electronic information. As a result, the electronic information appears to be part of the real world environment as perceived by a user. In an example, augmented reality technology further provides a user interface to interact with the electronic information that is overlaid in the enhanced real world environment.

A augmented reality (AR) system enables real and virtual environments to be combined in varying degrees to facilitate interactions from a user in a real time manner. Such an AR system, as described herein, therefore can include various possible combinations of real and virtual environments, including augmented reality that primarily includes real elements and is closer to a real environment than a virtual environment (e.g., without real elements). In this manner, a real environment can be connected with a virtual environment by the AR system. A user immersed in an AR environment can navigate through such an environment and the AR system can track the user's viewpoint to provide a visualization based on how the user is situated in the environment. Augmented reality (AR) experiences can be provided in a messaging client application (or the messaging system) as described in embodiments herein.

Embodiments of the subject technology described herein enable various operations involving AR content for capturing and modifying such content with a given electronic device, such as a wearable headset device (e.g., a given eyewear device) and a mobile computing device.

Messaging systems are frequently utilized and are increasingly leveraged by users of mobile computing devices, in various settings, to provide different types of functionality in a convenient manner. As described herein, the subject messaging system comprises practical applications that provide improvements in capturing image data and rendering AR content (e.g., images, videos, and the like) based on the captured image data by at least providing technical improvements with capturing image data using power and resource constrained electronic devices. Such improvements in capturing image data are enabled by techniques provided by the subject technology, which reduce latency and increase efficiency in processing captured image data thereby also reducing power consumption in the capturing devices.

As discussed further herein, the subject infrastructure supports the creation and sharing of interactive media, referred to herein as messages including 3D content or AR effects, throughout various components of a messaging system. In example embodiments described herein, messages can enter the system from a live camera or via from storage (e.g., where messages including 3D content and/or AR effects are stored in memory or a database). The subject system supports motion sensor input, and loading of external effects and asset data.

As referred to herein, the phrase "augmented reality experience," "augmented reality content item," "augmented reality content generator" includes or refers to various image processing operations corresponding to an image modification, filter, AR content generators, media overlay, transformation, and the like, and additionally can include playback of audio or music content during presentation of AR content or media content, as described further herein.

FIG. 1 is a block diagram showing an example messaging system 100 for exchanging data (e.g., messages and associated content) over a network. The messaging system 100 includes multiple instances of a client device 102, each of which hosts a number of applications including a messaging client application 104. Each messaging client application 104 is communicatively coupled to other instances of the messaging client application 104 and a messaging server system 108 via a network 106 (e.g., the Internet).

A messaging client application 104 is able to communicate and exchange data with another messaging client application 104 and with the messaging server system 108 via the network 106. The data exchanged between messaging client application 104, and between a messaging client application 104 and the messaging server system 108, includes functions (e.g., commands to invoke functions) as well as payload data (e.g., text, audio, video or other multimedia data).

The messaging system 100 includes an eyewear device 150, which hosts an eyewear system 160, among other applications. The eyewear device 150 is communicatively coupled to the client device 102 via the network 106 (which may include via a dedicated short-range communication path, such as a Bluetooth™ or Wi-Fi direct connection).

The eyewear device 150 may be a head mounted portable system, worn by a user, that includes a display system capable of presenting a visualization of an augmented reality environment to the user (e.g., head mounted display device). The eyewear device 150 may be powered with a battery of some kind. In an example, the display system controlled by the eyewear system 160 of the eyewear device 150 provides a stereoscopic presentation of the augmented reality environment, enabling a three-dimensional visual display of a rendering of a particular scene, to the user. Further, the eyewear device 150 may include various sensors including, but not limited to, cameras, image sensors, touch sensors, microphones, inertial measurement units (IMU), heart rate, temperature, among other types of sensors. Moreover, the eyewear device 150 may include hardware elements that can receive user input such as hardware buttons or switches. User input detected by such sensors and/or hardware elements correspond to various input modalities to initiate a particular operation(s). For example, such input modalities may include, but not limited to, facial tracking, eye tracking (e.g., gaze direction), hand tracking, gesture tracking, biometric readings (e.g., heart rate, pulse, pupil dilation, breath, temperature, electroencephalogram, olfactory), recognizing speech or audio (e.g., particular hotwords), and activating buttons or switches, etc.

The eyewear device 150 may be communicatively coupled to a base device such as the client device 102. Such a base device may, in general, include more computing resources and/or available power in comparison with the eyewear device 150. In an example, the eyewear device 150 may operate in various modes. For instance, the eyewear device 150 can operate in a standalone mode independent of any base device.

The eyewear device 150 may also operate in a wireless tethered mode (e.g., connected via a wireless connection with a base device such as client device 102), working in conjunction with a given base device. When the eyewear device 150 operates in the wireless tethered mode, a least a portion of processing user inputs and/or rendering the augmented reality environment may be offloaded to the base device thereby reducing processing burdens on the eyewear device 150. For instance, in an implementation, the eyewear device 150 works in conjunction with the client device 102 to generate an augmented reality environment including physical and/or virtual objects that enables different forms of interaction (e.g., visual, auditory, and/or physical or tactile interaction) between the user and the generated augmented reality environment in a real-time manner. In an example, the eyewear device 150 provides a rendering of a scene corresponding to the augmented reality environment that can be perceived by the user and interacted with in a real-time manner. Additionally, as part of presenting the rendered scene, the eyewear device 150 may provide sound, haptic, or tactile feedback to the user. The content of a given rendered scene may be dependent on available processing capability, network availability and capacity, available battery power, and current system workload.

In an implementation, the eyewear system 160 generates a message including a recording of a real environment and generates an augmented reality environment including two-dimensional (2D) video for sharing and playback. In another implementation, the eyewear system 160 generates a message, and subsequently generates a three-dimensional (3D) representation merging information from all sensors and/or combining recording with other users' messages (e.g., different point of views (POVs)). It is further appreciated that the client device 102 can also generate such augmented reality environments either working in conjunction with the eyewear device 150 or independently of the eyewear device 150.

The eyewear system 160 automatically or selectively moves augmented reality or virtual reality content from one virtual position to another as the user moves around the eyewear device 150. For example, the user or wearer of the eyewear device 150 may initially be looking at a first portion of a real-world environment (e.g., a first room in a house). The user may provide input (e.g., using a client device 102 or a voice activated or touch activated interface of the eyewear device 150) to launch or access virtual content that includes one or more objects.

The messaging server system 108 provides server-side functionality via the network 106 to a particular messaging client application 104. While certain functions of the messaging system 100 are described herein as being performed by either a messaging client application 104 or by the messaging server system 108, the location of certain functionality either within the messaging client application 104 or the messaging server system 108 is a design choice. For example, it may be technically preferable to initially deploy certain technology and functionality within the messaging server system 108, but to later migrate this technology and functionality to the messaging client application 104 where a client device 102 has a sufficient processing capacity.

The messaging server system 108 supports various services and operations that are provided to the messaging client application 104. Such operations include transmitting data to, receiving data from, and processing data generated by the messaging client application 104. This data may include, message content, client device information, geolocation information, media annotation and overlays, message content persistence conditions, social network information, and live event information, as examples. Data exchanges within the messaging system 100 are invoked and controlled through functions available via user interfaces (UIs) of the messaging client application 104.

Turning now specifically to the messaging server system 108, an Application Program Interface (API) server 110 is coupled to, and provides a programmatic interface to, an application server 112. The application server 112 is communicatively coupled to a database server 118, which facilitates access to a database 120 in which is stored data associated with messages processed by the application server 112.

The Application Program Interface (API) server 110 receives and transmits message data (e.g., commands and message payloads) between the client device 102 and the application server 112. Specifically, the Application Program Interface (API) server 110 provides a set of interfaces (e.g., routines and protocols) that can be called or queried by the messaging client application 104 in order to invoke functionality of the application server 112. The Application Program Interface (API) server 110 exposes various functions supported by the application server 112, including account registration, login functionality, the sending of messages, via the application server 112, from a particular messaging client application 104 to another messaging client application 104, the sending of media files (e.g., images or video) from a messaging client application 104 to the messaging server application 114, and for possible access by another messaging client application 104, the setting of a collection of media data (e.g., story), the retrieval of a list of friends of a user of a client device 102, the retrieval of such collections, the retrieval of messages and content, the adding and deletion of friends to a social graph, the location of friends within a social graph, and opening an application event (e.g., relating to the messaging client application 104).

The application server 112 hosts a number of applications and subsystems, including a messaging server application 114, an image processing system 116 and a social network system 122. The messaging server application 114 implements a number of message processing technologies and functions, particularly related to the aggregation and other processing of content (e.g., textual and multimedia content) included in messages received from multiple instances of the messaging client application 104. As will be described in further detail, the text and media content from multiple sources may be aggregated into collections of content (e.g., called stories or galleries). These collections are then made available, by the messaging server application 114, to the messaging client application 104. Other processor and memory intensive processing of data may also be performed server-side by the messaging server application 114, in view of the hardware requirements for such processing.

The application server 112 also includes an image processing system 116 that is dedicated to performing various image processing operations, typically with respect to images or video received within the payload of a message at the messaging server application 114.

Figure 3:
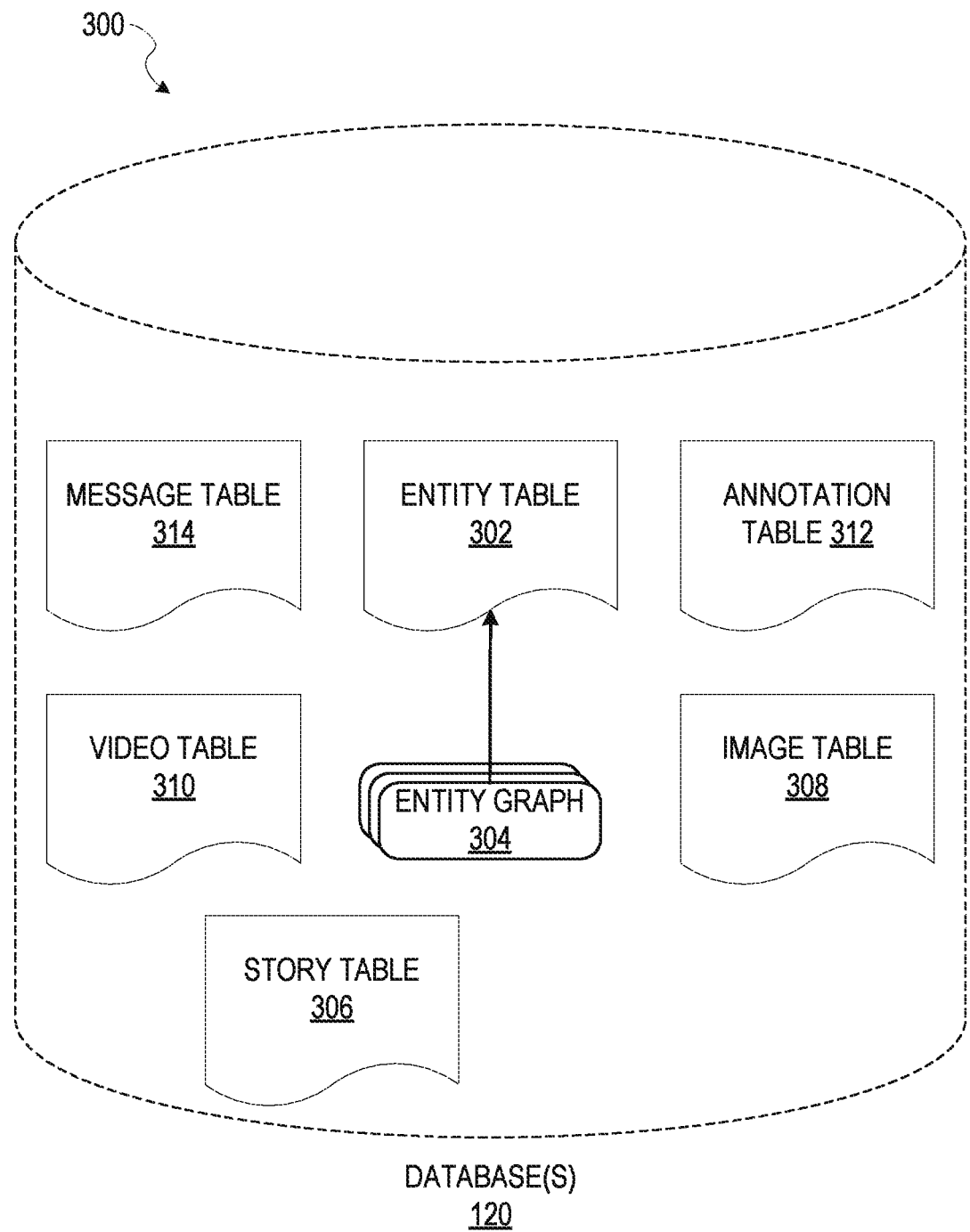
FIG. 3 is a diagrammatic representation of a data structure as maintained in a database, in accordance with some example embodiments.

The social network system 122 supports various social networking functions services, and makes these functions and services available to the messaging server application 114. To this end, the social network system 122 maintains and accesses an entity graph 304 (as shown in FIG. 3) within the database 120. Examples of functions and services supported by the social network system 122 include the identification of other users of the messaging system 100 with which a particular user has relationships or is 'following', and also the identification of other entities and interests of a particular user.

The application server 112 is communicatively coupled to a database server 118, which facilitates access to a database 120 in which is stored data associated with messages processed by the messaging server application 114.

Figure 2:
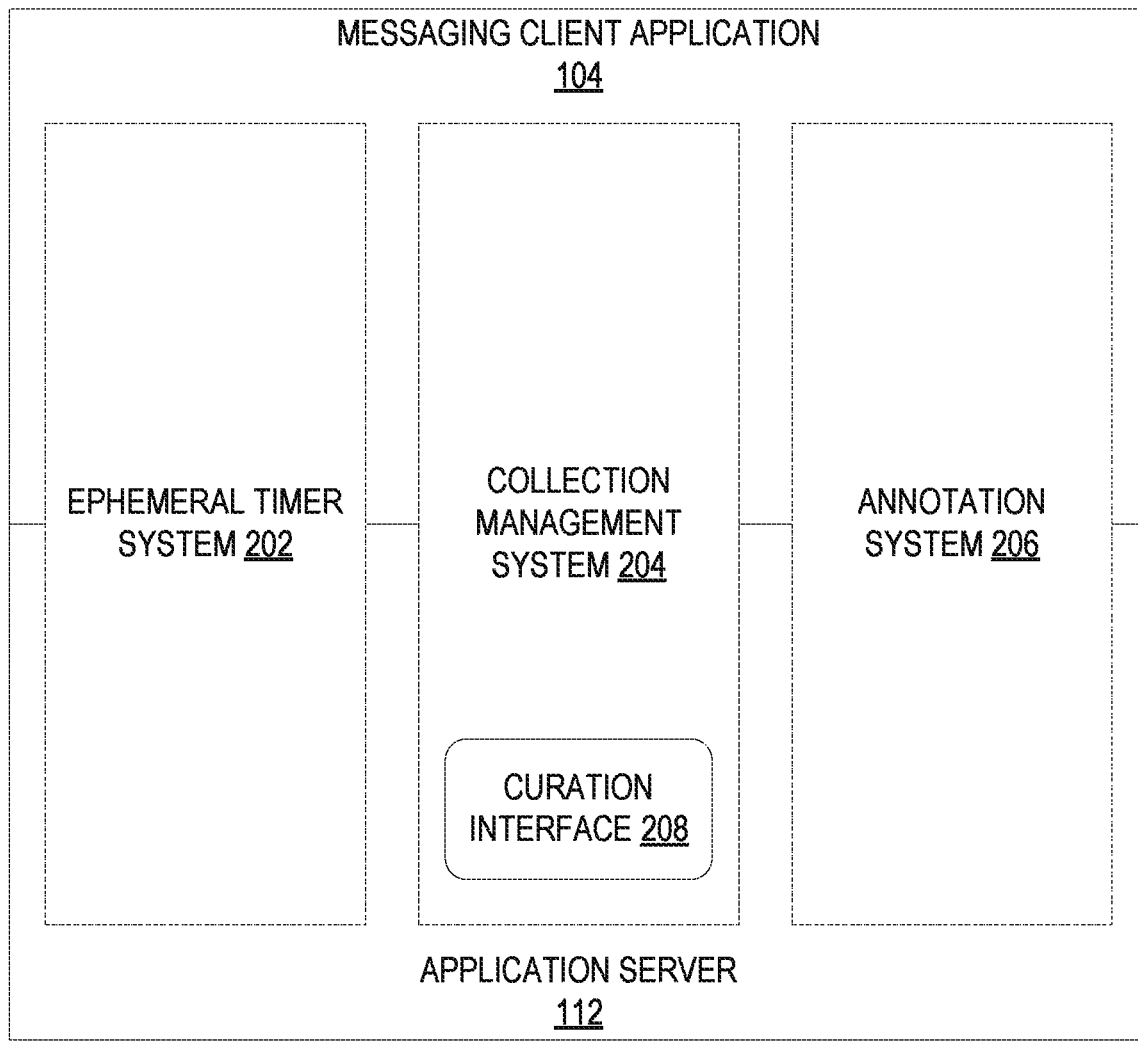
FIG. 2 is a diagrammatic representation of a messaging client application, in accordance with some example embodiments.

FIG. 2 is block diagram illustrating further details regarding the messaging system 100, according to example embodiments. Specifically, the messaging system 100 is shown to comprise the messaging client application 104 and the application server 112, which in turn embody a number of some subsystems, namely an ephemeral timer system 202, a collection management system 204 and an annotation system 206.

The ephemeral timer system 202 is responsible for enforcing the temporary access to content permitted by the messaging client application 104 and the messaging server application 114. To this end, the ephemeral timer system 202 incorporates a number of timers that, based on duration and display parameters associated with a message, or collection of messages (e.g., a story), selectively display and enable access to messages and associated content via the messaging client application 104. Further details regarding the operation of the ephemeral timer system 202 are provided below.

The collection management system 204 is responsible for managing collections of media (e.g., collections of text, image video and audio data). In some examples, a collection of content (e.g., messages, including images, video, text and audio) may be organized into an 'event gallery' or an 'event story.' Such a collection may be made available for a specified time period, such as the duration of an event to which the content relates. For example, content relating to a music concert may be made available as a 'story' for the duration of that music concert. The collection management system 204 may also be responsible for publishing an icon that provides notification of the existence of a particular collection to the user interface of the messaging client application 104.

The collection management system 204 furthermore includes a curation interface 208 that allows a collection manager to manage and curate a particular collection of content. For example, the curation interface 208 enables an event organizer to curate a collection of content relating to a specific event (e.g., delete inappropriate content or redundant messages). Additionally, the collection management system 204 employs machine vision (or image recognition technology) and content rules to automatically curate a content collection. In certain embodiments, compensation may be paid to a user for inclusion of user-generated content into a collection. In such cases, the curation interface 208 operates to automatically make payments to such users for the use of their content.

The annotation system 206 provides various functions that enable a user to annotate or otherwise modify or edit media content associated with a message. For example, the annotation system 206 provides functions related to the generation and publishing of media overlays for messages processed by the messaging system 100. The annotation system 206 operatively supplies a media overlay or supplementation (e.g., an image filter) to the messaging client application 104 based on a geolocation of the client device 102. In another example, the annotation system 206 operatively supplies a media overlay to the messaging client application 104 based on other information, such as social network information of the user of the client device 102. A media overlay may include audio and visual content and visual effects. Examples of audio and visual content include pictures, texts, logos, animations, and sound effects. An example of a visual effect includes color overlaying. The audio and visual content or the visual effects can be applied to a media content item (e.g., a photo) at the client device 102. For example, the media overlay may include text that can be overlaid on top of a photograph taken by the client device 102. In another example, the media overlay includes an identification of a location overlay (e.g., Venice beach), a name of a live event, or a name of a merchant overlay (e.g., Beach Coffee House). In another example, the annotation system 206 uses the geolocation of the client device 102 to identify a media overlay that includes the name of a merchant at the geolocation of the client device 102. The media overlay may include other indicia associated with the merchant. The media overlays may be stored in the database 120 and accessed through the database server 118.

In one example embodiment, the annotation system 206 provides a user-based publication platform that enables users to select a geolocation on a map, and upload content associated with the selected geolocation. The user may also specify circumstances under which a particular media overlay should be offered to other users. The annotation system 206 generates a media overlay that includes the uploaded content and associates the uploaded content with the selected geolocation.

In another example embodiment, the annotation system 206 provides a merchant-based publication platform that enables merchants to select a particular media overlay associated with a geolocation via a bidding process. For example, the annotation system 206 associates the media overlay of a highest bidding merchant with a corresponding geolocation for a predefined amount of time.

FIG. 3 is a schematic diagram illustrating data structures 300 which may be stored in the database 120 of the messaging server system 108, according to certain example embodiments. While the content of the database 120 is shown to comprise a number of tables, it will be appreciated that the data could be stored in other types of data structures (e.g., as an object-oriented database).

The database 120 includes message data stored within a message table 314. The entity table 302 stores entity data, including an entity graph 304. Entities for which records are maintained within the entity table 302 may include individuals, corporate entities, organizations, objects, places, events, etc. Regardless of type, any entity regarding which the messaging server system 108 stores data may be a recognized entity. Each entity is provided with a unique identifier, as well as an entity type identifier (not shown).

The entity graph 304 furthermore stores information regarding relationships and associations between entities. Such relationships may be social, professional (e.g., work at a common corporation or organization) interested-based or activity-based, merely for example.

The database 120 also stores annotation data, in the example form of filters, in an annotation table 312. Filters for which data is stored within the annotation table 312 are associated with and applied to videos (for which data is stored in a video table 310) and/or images (for which data is stored in an image table 308). Filters, in one example, are overlays that are displayed as overlaid on an image or video during presentation to a recipient user. Filters may be of varies types, including user-selected filters from a gallery of filters presented to a sending user by the messaging client application 104 when the sending user is composing a message. Other types of filters include geolocation filters (also known as geo-filters) which may be presented to a sending user based on geographic location. For example, geolocation filters specific to a neighborhood or special location may be presented within a user interface by the messaging client application 104, based on geolocation information determined by a GPS unit of the client device 102. Another type of filer is a data filer, which may be selectively presented to a sending user by the messaging client application 104, based on other inputs or information gathered by the client device 102 during the message creation process. Example of data filters include current temperature at a specific location, a current speed at which a sending user is traveling, battery life for a client device 102, or the current time.

Other annotation data that may be stored within the image table 308 are augmented reality content generators (e.g., corresponding to applying AR content generators, augmented reality experiences, or augmented reality content items). An augmented reality content generator may be a real-time special effect and sound that may be added to an image or a video.

As described above, augmented reality content generators, augmented reality content items, overlays, image transformations, AR images and similar terms refer to modifications that may be made to videos or images. This includes real-time modification which modifies an image as it is captured using a device sensor and then displayed on a screen of the device with the modifications. This also includes modifications to stored content, such as video clips in a gallery that may be modified. For example, in a device with access to multiple augmented reality content generators, a user can use a single video clip with multiple augmented reality content generators to see how the different augmented reality content generators will modify the stored clip. For example, multiple augmented reality content generators that apply different pseudorandom movement models can be applied to the same content by selecting different augmented reality content generators for the content. Similarly, real-time video capture may be used with an illustrated modification to show how video images currently being captured by sensors of a device would modify the captured data. Such data may simply be displayed on the screen and not stored in memory, or the content captured by the device sensors may be recorded and stored in memory with or without the modifications (or both). In some systems, a preview feature can show how different augmented reality content generators will look within different windows in a display at the same time. This can, for example, enable multiple windows with different pseudorandom animations to be viewed on a display at the same time.

Data and various systems using augmented reality content generators or other such transform systems to modify content using this data can thus involve detection of objects (e.g., faces, hands, bodies, cats, dogs, surfaces, objects, etc.), tracking of such objects as they leave, enter, and move around the field of view in video frames, and the modification or transformation of such objects as they are tracked. In various embodiments, different methods for achieving such transformations may be used. For example, some embodiments may involve generating a three-dimensional mesh model of the object or objects, and using transformations and animated textures of the model within the video to achieve the transformation. In other embodiments, tracking of points on an object may be used to place an image or texture (which may be two dimensional or three dimensional) at the tracked position. In still further embodiments, neural network analysis of video frames may be used to place images, models, or textures in content (e.g., images or frames of video). Augmented reality content generators thus refer both to the images, models, and textures used to create transformations in content, as well as to additional modeling and analysis information needed to achieve such transformations with object detection, tracking, and placement.

Real-time video processing can be performed with any kind of video data (e.g., video streams, video files, etc.) saved in a memory of a computerized system of any kind. For example, a user can load video files and save them in a memory of a device, or can generate a video stream using sensors of the device. Additionally, any objects can be processed using a computer animation model, such as a human's face and parts of a human body, animals, or non-living things such as chairs, cars, or other objects.

In some embodiments, when a particular modification is selected along with content to be transformed, elements to be transformed are identified by the computing device, and then detected and tracked if they are present in the frames of the video. The elements of the object are modified according to the request for modification, thus transforming the frames of the video stream. Transformation of frames of a video stream can be performed by different methods for different kinds of transformation. For example, for transformations of frames mostly referring to changing forms of object's elements characteristic points for each of element of an object are calculated (e.g., using an Active Shape Model (ASM) or other known methods). Then, a mesh based on the characteristic points is generated for each of the at least one element of the object. This mesh used in the following stage of tracking the elements of the object in the video stream. In the process of tracking, the mentioned mesh for each element is aligned with a position of each element. Then, additional points are generated on the mesh. A first set of first points is generated for each element based on a request for modification, and a set of second points is generated for each element based on the set of first points and the request for modification. Then, the frames of the video stream can be transformed by modifying the elements of the object on the basis of the sets of first and second points and the mesh. In such method, a background of the modified object can be changed or distorted as well by tracking and modifying the background.

In one or more embodiments, transformations changing some areas of an object using its elements can be performed by calculating of characteristic points for each element of an object and generating a mesh based on the calculated characteristic points. Points are generated on the mesh, and then various areas based on the points are generated. The elements of the object are then tracked by aligning the area for each element with a position for each of the at least one element, and properties of the areas can be modified based on the request for modification, thus transforming the frames of the video stream. Depending on the specific request for modification properties of the mentioned areas can be transformed in different ways. Such modifications may involve changing color of areas; removing at least some part of areas from the frames of the video stream; including one or more new objects into areas which are based on a request for modification; and modifying or distorting the elements of an area or object. In various embodiments, any combination of such modifications or other similar modifications may be used. For certain models to be animated, some characteristic points can be selected as control points to be used in determining the entire state-space of options for the model animation.

In some embodiments of a computer animation model to transform image data using face detection, the face is detected on an image with use of a specific face detection algorithm (e.g., Viola-Jones). Then, an Active Shape Model (ASM) algorithm is applied to the face region of an image to detect facial feature reference points.

In other embodiments, other methods and algorithms suitable for face detection can be used. For example, in some embodiments, features are located using a landmark which represents a distinguishable point present in most of the images under consideration. For facial landmarks, for example, the location of the left eye pupil may be used. In an initial landmark is not identifiable (e.g., if a person has an eyepatch), secondary landmarks may be used. Such landmark identification procedures may be used for any such objects. In some embodiments, a set of landmarks forms a shape. Shapes can be represented as vectors using the coordinates of the points in the shape. One shape is aligned to another with a similarity transform (allowing translation, scaling, and rotation) that minimizes the average Euclidean distance between shape points. The mean shape is the mean of the aligned training shapes.

In some embodiments, a search for landmarks from the mean shape aligned to the position and size of the face determined by a global face detector is started. Such a search then repeats the steps of suggesting a tentative shape by adjusting the locations of shape points by template matching of the image texture around each point and then conforming the tentative shape to a global shape model until convergence occurs. In some systems, individual template matches are unreliable and the shape model pools the results of the weak template matchers to form a stronger overall classifier. The entire search is repeated at each level in an image pyramid, from coarse to fine resolution.

Embodiments of a transformation system can capture an image or video stream on a client device (e.g., the client device 102) and perform complex image manipulations locally on the client device 102 while maintaining a suitable user experience, computation time, and power consumption. The complex image manipulations may include size and shape changes, emotion transfers (e.g., changing a face from a frown to a smile), state transfers (e.g., aging a subject, reducing apparent age, changing gender), style transfers, graphical element application, and any other suitable image or video manipulation implemented by a convolutional neural network that has been configured to execute efficiently on the client device 102.

In some example embodiments, a computer animation model to transform image data can be used by a system where a user may capture an image or video stream of the user (e.g., a selfie) using a client device 102 having a neural network operating as part of a messaging client application 104 operating on the client device 102. The transform system operating within the messaging client application 104 determines the presence of a face within the image or video stream and provides modification icons associated with a computer animation model to transform image data, or the computer animation model can be present as associated with an interface described herein. The modification icons include changes which may be the basis for modifying the user's face within the image or video stream as part of the modification operation. Once a modification icon is selected, the transform system initiates a process to convert the image of the user to reflect the selected modification icon (e.g., generate a smiling face on the user). In some embodiments, a modified image or video stream may be presented in a graphical user interface displayed on the mobile client device as soon as the image or video stream is captured and a specified modification is selected. The transform system may implement a complex convolutional neural network on a portion of the image or video stream to generate and apply the selected modification. That is, the user may capture the image or video stream and be presented with a modified result in real time or near real time once a modification icon has been selected. Further, the modification may be persistent while the video stream is being captured and the selected modification icon remains toggled. Machine taught neural networks may be used to enable such modifications.

In some embodiments, the graphical user interface, presenting the modification performed by the transform system, may supply the user with additional interaction options. Such options may be based on the interface used to initiate the content capture and selection of a particular computer animation model (e.g., initiation from a content creator user interface). In various embodiments, a modification may be persistent after an initial selection of a modification icon. The user may toggle the modification on or off by tapping or otherwise selecting the face being modified by the transformation system and store it for later viewing or browse to other areas of the imaging application. Where multiple faces are modified by the transformation system, the user may toggle the modification on or off globally by tapping or selecting a single face modified and displayed within a graphical user interface. In some embodiments, individual faces, among a group of multiple faces, may be individually modified or such modifications may be individually toggled by tapping or selecting the individual face or a series of individual faces displayed within the graphical user interface.

In some example embodiments, a graphical processing pipeline architecture is provided that enables different augmented reality experiences (e.g., AR content generators) to be applied in corresponding different layers. Such a graphical processing pipeline provides an extensible rendering engine for providing multiple augmented reality experiences that are included in a composite media (e.g., image or video) or composite AR content for rendering by the messaging client application 104 (or the messaging system 100).

As mentioned above, the video table 310 stores video data which, in one embodiment, is associated with messages for which records are maintained within the message table 314. Similarly, the image table 308 stores image data associated with messages for which message data is stored in the entity table 302. The entity table 302 may associate various annotations from the annotation table 312 with various images and videos stored in the image table 308 and the video table 310.

A story table 306 stores data regarding collections of messages and associated image, video, or audio data, which are compiled into a collection (e.g., a story or a gallery). The creation of a particular collection may be initiated by a particular user (e.g., each user for which a record is maintained in the entity table 302). A user may create a 'personal story' in the form of a collection of content that has been created and sent/broadcast by that user. To this end, the user interface of the messaging client application 104 may include an icon that is user-selectable to enable a sending user to add specific content to his or her personal story.

A collection may also constitute a 'live story,' which is a collection of content from multiple users that is created manually, automatically, or using a combination of manual and automatic techniques. For example, a 'live story' may constitute a curated stream of user-submitted content from varies locations and events. Users whose client devices have location services enabled and are at a common location event at a particular time may, for example, be presented with an option, via a user interface of the messaging client application 104, to contribute content to a particular live story. The live story may be identified to the user by the messaging client application 104, based on his or her location. The end result is a 'live story' told from a community perspective.

A further type of content collection is known as a 'location story', which enables a user whose client device 102 is located within a specific geographic location (e.g., on a college or university campus) to contribute to a particular collection. In some embodiments, a contribution to a location story may require a second degree of authentication to verify that the end user belongs to a specific organization or other entity (e.g., is a student on the university campus).

Figure 4:
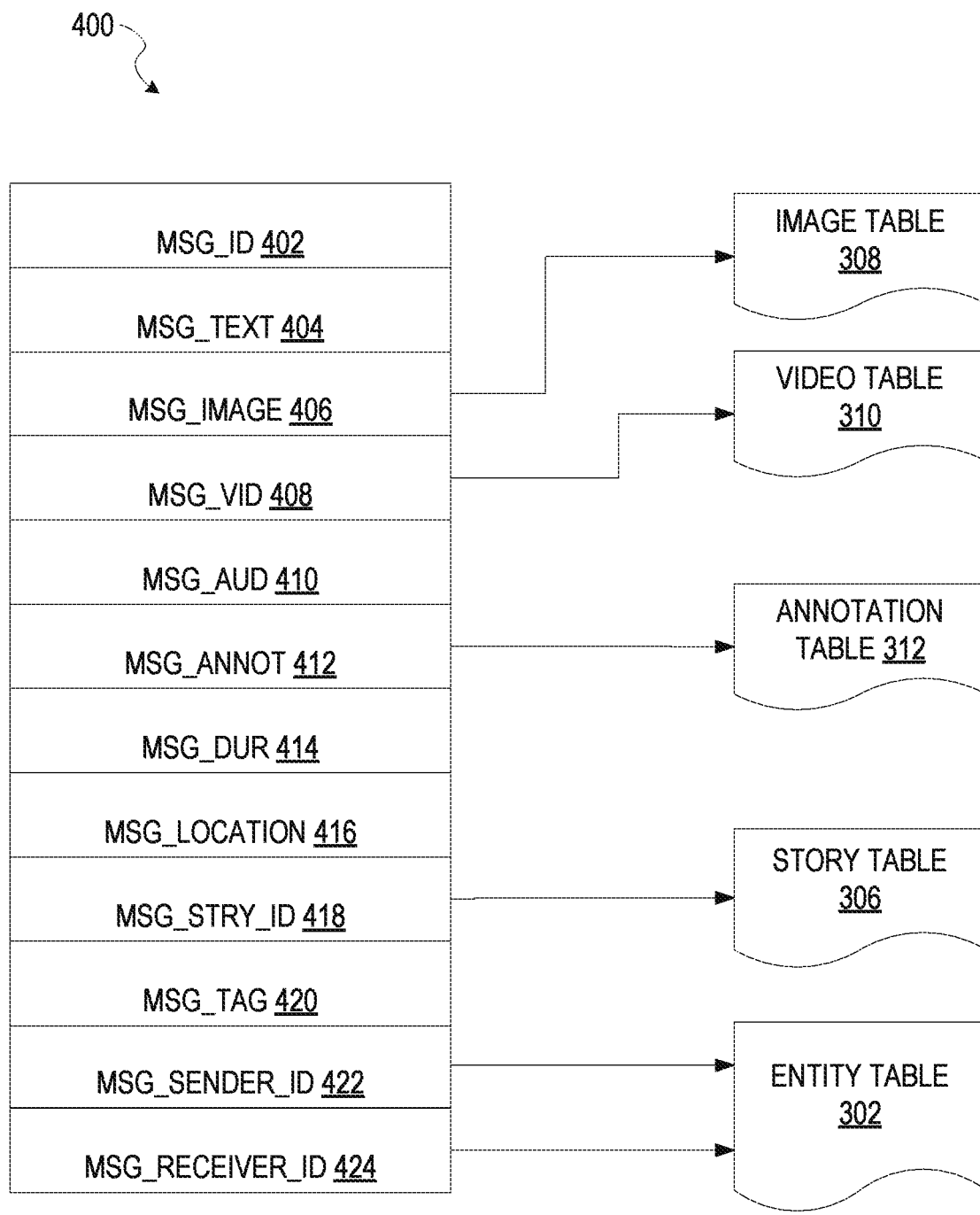
FIG. 4 is a diagrammatic representation of a message, in accordance with some example embodiments.

FIG. 4 is a schematic diagram illustrating a structure of a message 400, according to some embodiments, generated by a messaging client application 104 or the eyewear system 160 for communication to a further messaging client application 104 or the messaging server application 114. The content of a particular message 400 is used to populate the message table 314 stored within the database 120, accessible by the messaging server application 114. Similarly, the content of a message 400 is stored in memory as 'in-transit' or 'in-flight' data of the client device 102 or the application server 112. The message 400 is shown to include the following components:

A message identifier 402: a unique identifier that identifies the message 400.

A message text payload 404: text, to be generated by a user via a user interface of the client device 102 and that is included in the message 400.

A message image payload 406: image data, captured by a camera component of a client device 102 or retrieved from a memory component of a client device 102, and that is included in the message 400.

A message video payload 408: video data, captured by a camera component or retrieved from a memory component of the client device 102 and that is included in the message 400.

A message audio payload 410: audio data, captured by a microphone or retrieved from a memory component of the client device 102, and that is included in the message 400.

A message annotations 412: annotation data (e.g., filters, stickers or other enhancements) that represents annotations to be applied to message image payload 406, message video payload 408, or message audio payload 410 of the message 400.

A message duration parameter 414: parameter value indicating, in seconds, the amount of time for which content of the message (e.g., the message image payload 406, message video payload 408, message audio payload 410) is to be presented or made accessible to a user via the messaging client application 104.

A message geolocation parameter 416: geolocation data (e.g., latitudinal and longitudinal coordinates) associated with the content payload of the message. Multiple message geolocation parameter 416 values may be included in the payload, each of these parameter values being associated with respect to content items included in the content (e.g., a specific image into within the message image payload 406, or a specific video in the message video payload 408).

A message story identifier 418: identifier values identifying one or more content collections (e.g., 'stories') with which a particular content item in the message image payload 406 of the message 400 is associated. For example, multiple images within the message image payload 406 may each be associated with multiple content collections using identifier values.

A message tag 420: each message 400 may be tagged with multiple tags, each of which is indicative of the subject matter of content included in the message payload. For example, where a particular image included in the message image payload 406 depicts an animal (e.g., a lion), a tag value may be included within the message tag 420 that is indicative of the relevant animal. Tag values may be generated manually, based on user input, or may be automatically generated using, for example, image recognition.

A message sender identifier 422: an identifier (e.g., a messaging system identifier, email address, or device identifier) indicative of a user of the client device 102 on which the message 400 was generated and from which the message 400 was sent A message receiver identifier 424: an identifier (e.g., a messaging system identifier, email address, or device identifier) indicative of a user of the client device 102 to which the message 400 is addressed.

The contents (e.g., values) of the various components of message 400 may be pointers to locations in tables within which content data values are stored. For example, an image value in the message image payload 406 may be a pointer to (or address of) a location within an image table 308. Similarly, values within the message video payload 408 may point to data stored within a video table 310, values stored within the message annotations 412 may point to data stored in an annotation table 312, values stored within the message story identifier 418 may point to data stored in a story table 306, and values stored within the message sender identifier 422 and the message receiver identifier 424 may point to user records stored within an entity table 302.

Figure 5:
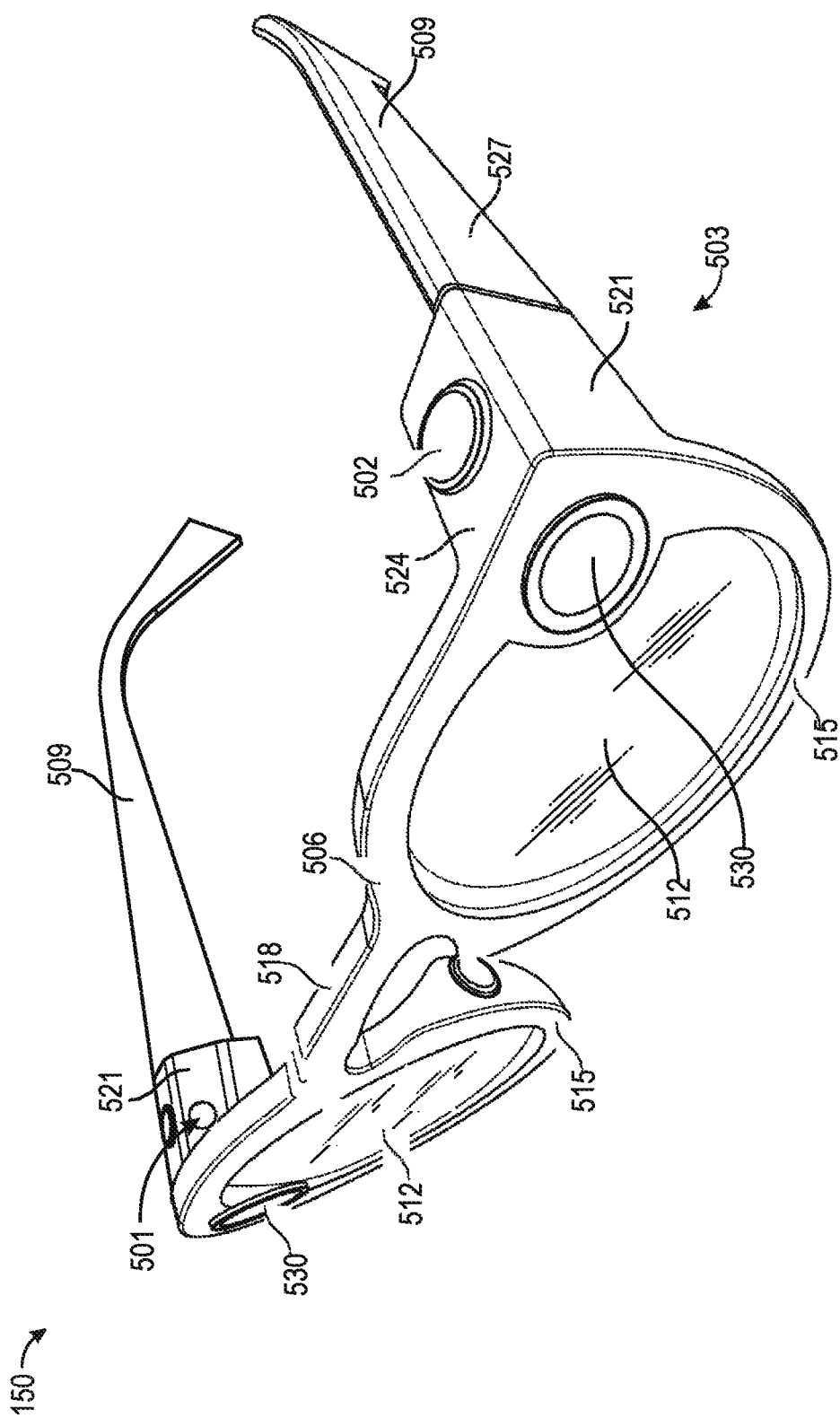
FIG. 5 shows a front perspective view of an eyewear device in the form of a pair of smart glasses that include a eyewear system according to one example embodiment.

FIG. 5 shows a front perspective view of an eyewear device 150 in the form of a pair of smart glasses that include a eyewear system 160 according to one example embodiment. The eyewear device 150 includes a body 503 comprising a front piece or frame 506 and a pair of temples 509 connected to the frame 506 for supporting the frame 506 in position on a user's face when the eyewear device 150 is worn. The frame 506 can be made from any suitable material such as plastics or metal, including any suitable shape memory alloy.

The eyewear device 150 includes a pair of optical elements in the form of a pair of lenses 512 held by corresponding optical element holders in the form of a pair of rims 515 forming part of the frame 506. The rims 515 are connected by a bridge 518. In other embodiments, one or both of the optical elements can be a display, a display assembly, or a lens and display combination.

The frame 506 includes a pair of end pieces 521 defining lateral end portions of the frame 506. In this example, a variety of electronics components are housed in one or both of the end pieces 521. The temples 509 are coupled to the respective end pieces 521. In this example, the temples 509 are coupled to the frame 506 by respective hinges so as to be hingedly movable between a wearable mode and a collapsed mode in which the temples 509 are pivoted towards the frame 506 to lie substantially flat against it. In other embodiments, the temples 509 can be coupled to the frame 506 by any suitable means, or can be rigidly or fixedly secured to the frame 506 so as to be integral therewith.

Each of the temples 509 that includes a front portion of that is coupled to the frame 506 and any suitable rear portion for coupling to the ear of the user, such as the curves or cute piece illustrated in the example embodiment of FIG. 5. In some embodiments, the frame 506 is formed of a single piece of material, so as to have a unitary or monolithic construction. In some embodiments, the whole of the body 503 (including both the frame 506 and the temples 509) can be of the unitary or monolithic construction.

The eyewear device 150 has onboard electronics components including a computing device, such as a computer 524, or low power processor, which can in different embodiments be of any suitable type so as to be carried by the body 503. In some embodiments, the computer 524 is at least partially housed in one or both of the temples 509. In the present embodiment, various components of the computer 524 are housed in the lateral end pieces 521 of the frame 506. The computer 524 includes one or more processors with memory (e.g., a volatile storage device, such as random access memory or registers), a storage device (e.g., a non-volatile storage device), wireless communication circuitry (e.g., BLE communication devices and/or WiFi direct devices), and a power source. The computer 524 comprises low-power circuitry, high-speed circuitry, and, in some embodiments, a display processor. Various embodiments may include these elements in different configurations or integrated together in different ways.

The computer 524 additionally includes a battery 527 or other suitable portable power supply. In one embodiment, the battery 527 is disposed in one of the temples 509. In the eyewear device 150 shown in FIG. 5, the battery 527 is shown as being disposed in one of the end pieces 521, being electrically coupled to the remainder of the computer 524 housed in the corresponding end piece 521.

The eyewear device 150 is camera-enabled, in this example comprising a camera 530 mounted in one of the end pieces 521 and facing forwards so as to be aligned more or less with the direction of view of a wearer of the eyewear device 150. The camera 530 is configured to capture digital images (also referred to herein as digital photographs or pictures) as well as digital video content. Operation of the camera 530 is controlled by a camera controller provided by the computer 524, image data representative of images or video captured by the camera 530 being temporarily stored on a memory forming part of the computer 524. In some embodiments, the eyewear device 150 can have a pair of cameras 530, e.g. housed by the respective end pieces 521.

As will be described in greater detail below, the onboard computer 524 and the lenses 512 are configured together to provide a eyewear system 160 that automatically and selectively re-centers virtual content to bring the virtual content to within view of the lenses 512 by moving the virtual content from a first virtual location to a second virtual location. Specifically, the lenses 512 can display virtual content or one or more virtual objects. This makes it appear to the user that the virtual content is integrated within a real-world environment that the user views through the lenses 512. In some embodiments, the virtual content is received from the client device 102. In some embodiments, the virtual content is received directly from the application server 112.

The eyewear device 150 includes an accelerometer and a touch interface and a voice command system. Based on input received by the eyewear device 150 from the accelerometer and a touch interface and the voice command system, the eyewear device 150 can control user interaction with the virtual content. In one example, the user interaction can control playback of content that is presented on the lenses 512. In another example, the user interaction can navigate through a playlist or music or video library. In another example, the user interaction can navigate through a conversation the user is involved in, such as by scrolling through various three-dimensional or two-dimensional conversation elements (e.g., chat bubbles) and selecting individual conversation elements to respond to generate messages to transmit to participants of the conversation.

The eyewear system 160 (which can be implemented by the computer 524) assigns virtual content to virtual locations. The eyewear system 160 monitors the current virtual location that is within view of a real-world environment. The eyewear system 160 retrieves virtual content for display that is within a specified range of the current virtual location that is within view. As the eyewear device 150 is moved around to be directed to a new portion of the real-world environment, associated with a different set of virtual locations, the eyewear system 160 excludes any virtual content that is not within range of the different set of virtual locations. For example, as the eyewear device 150 is moved around to be directed to a new portion of the real-world environment that does not overlap with the previously displayed portion of the real-world environment, the eyewear system 160 excludes any virtual content that is not within range of the different set of virtual locations.

The eyewear system 160 can receive a request to bring virtual content into a current view. In response, the eyewear system 160 updates the virtual location assigned and associated with the virtual content to be the virtual location that is associated with the current view of the real-world environment. As a result, the virtual content is now moved from being out of view to be included in the current view to allow the user to interact with the virtual content. In some cases, the user can only interact with virtual content that is within view of the lenses 512. If the user moves around to face another direction resulting in the virtual content going out of view, the user input no longer can control or interact with the previously displayed virtual content until the virtual content is brought back into view.

The eyewear device 150 further includes one or more communication devices, such as Bluetooth low energy (BLE) communication interface. Such BLE communication interface enables the eyewear device 150 to communicate wirelessly with the client device 102. Other forms of wireless communication can also be employed instead of, or in addition to, the BLE communication interface, such as a WiFi direct interface. The BLE communication interface implements a standard number of BLE communication protocols.

A first of the communications protocols implemented by the BLE interface of the eyewear device 150 enables an unencrypted link to be established between the eyewear device 150 and the client device 102. In this first protocol, the link-layer communication (the physical interface or medium) between the eyewear device 150 and the client device 102 includes unencrypted data. In this first protocol, the application layer (the communication layer operating on the physically exchanged data) encrypts and decrypts data that is physically exchanged in unencrypted form over the link layer of the BLE communication interface. In this way, data exchanged over the physical layer can freely be read by an eavesdropping device, but the eavesdropping device will not be able to decipher the data that is exchanged without performing a decryption operation in the application layer.

A second of the communications protocols implemented by the BLE interface of the eyewear device 150 enables an encrypted link to be established between the eyewear device 150 and the client device 102. In this second protocol, the link-layer communication (the physical interface) between the eyewear device 150 and the client device 102 receives data from the application layer and adds a first type of encryption to the data before exchanging the data over the physical medium. In this second protocol, the application layer (the communication layer operating on the physically exchanged data) may or may not use a second type of encryption to encrypt and decrypt data that is physically exchanged in encrypted form, using the first type of encryption, over the link layer of the BLE communication interface. Namely, data can be first encrypted by the application layer and then be further encrypted by the physical layer before being exchanged over the physical medium. Following the exchange over the physical medium, the data is then decrypted by the physical layer and then decrypted again (e.g., using a different type of encryption) by the application layer. In this way, data exchanged over the physical layer cannot be read by an eavesdropping device as the data is encrypted in the physical medium.

In some embodiments, the client device 102 communicates with the eyewear device 150 using the first protocol to exchange images or videos or virtual content between the messaging client 104 and the eyewear device 150.

As described above, media overlays, such as AR content generators, overlays, image transformations, AR images and similar terms refer to modifications that may be made to videos or images. This includes real-time modification which modifies an image as it is captured using a device sensor and then displayed on a screen of the device with the modifications. This also includes modifications to stored content, such as video clips in a gallery that may be modified. For example, in a device with access to multiple media overlays (e.g., AR content generators), a user can use a single video clip with multiple AR content generators to see how the different AR content generators will modify the stored clip. For example, multiple AR content generators that apply different pseudorandom movement models can be applied to the same content by selecting different AR content generators for the content. Similarly, real-time video capture may be used with an illustrated modification to show how video images currently being captured by sensors of a device would modify the captured data. Such data may simply be displayed on the screen and not stored in memory, or the content captured by the device sensors may be recorded and stored in memory with or without the modifications (or both). In some systems, a preview feature can show how different AR content generators will look within different windows in a display at the same time. This can, for example, enable multiple windows with different pseudorandom animations to be viewed on a display at the same time.

Data and various systems to use AR content generators or other such transform systems to modify content using this data can thus involve detection of objects (e.g. faces, hands, bodies, cats, dogs, surfaces, objects, etc.), tracking of such objects as they leave, enter, and move around the field of view in video frames, and the modification or transformation of such objects as they are tracked. In various embodiments, different methods for achieving such transformations may be used. For example, some embodiments may involve generating a three-dimensional mesh model of the object or objects, and using transformations and animated textures of the model within the video to achieve the transformation. In other embodiments, tracking of points on an object may be used to place an image or texture (which may be two dimensional or three dimensional) at the tracked position. In still further embodiments, neural network analysis of video frames may be used to place images, models, or textures in content (e.g. images or frames of video). Lens data thus refers both to the images, models, and textures used to create transformations in content, as well as to additional modeling and analysis information needed to achieve such transformations with object detection, tracking, and placement.

Real time video processing can be performed with any kind of video data, (e.g. video streams, video files, etc.) saved in a memory of a computerized system of any kind. For example, a user can load video files and save them in a memory of a device, or can generate a video stream using sensors of the device. Additionally, any objects can be processed using a computer animation model, such as a human's face and parts of a human body, animals, or non-living things such as chairs, cars, or other objects.

In some embodiments, when a particular modification is selected along with content to be transformed, elements to be transformed are identified by the computing device, and then detected and tracked if they are present in the frames of the video. The elements of the object are modified according to the request for modification, thus transforming the frames of the video stream. Transformation of frames of a video stream can be performed by different methods for different kinds of transformation. For example, for transformations of frames mostly referring to changing forms of object's elements characteristic points for each of element of an object are calculated (e.g. using an Active Shape Model (ASM) or other known methods). Then, a mesh based on the characteristic points is generated for each of the at least one element of the object. This mesh used in the following stage of tracking the elements of the object in the video stream. In the process of tracking, the mentioned mesh for each element is aligned with a position of each element. Then, additional points are generated on the mesh. A first set of first points is generated for each element based on a request for modification, and a set of second points is generated for each element based on the set of first points and the request for modification. Then, the frames of the video stream can be transformed by modifying the elements of the object on the basis of the sets of first and second points and the mesh. In such method a background of the modified object can be changed or distorted as well by tracking and modifying the background.

In one or more embodiments, transformations changing some areas of an object using its elements can be performed by calculating of characteristic points for each element of an object and generating a mesh based on the calculated characteristic points. Points are generated on the mesh, and then various areas based on the points are generated. The elements of the object are then tracked by aligning the area for each element with a position for each of the at least one element, and properties of the areas can be modified based on the request for modification, thus transforming the frames of the video stream. Depending on the specific request for modification properties of the mentioned areas can be transformed in different ways. Such modifications may involve: changing color of areas; removing at least some part of areas from the frames of the video stream; including one or more new objects into areas which are based on a request for modification; and modifying or distorting the elements of an area or object. In various embodiments, any combination of such modifications or other similar modifications may be used. For certain models to be animated, some characteristic points can be selected as control points to be used in determining the entire state-space of options for the model animation.

In some embodiments of a computer animation model to transform image data using face detection, the face is detected on an image with use of a specific face detection algorithm (e.g. Viola-Jones). Then, an Active Shape Model (ASM) algorithm is applied to the face region of an image to detect facial feature reference points.

In other embodiments, other methods and algorithms suitable for face detection can be used. For example, in some embodiments, features are located using a landmark which represents a distinguishable point present in most of the images under consideration. For facial landmarks, for example, the location of the left eye pupil may be used. In an initial landmark is not identifiable (e.g. if a person has an eyepatch), secondary landmarks may be used. Such landmark identification procedures may be used for any such objects. In some embodiments, a set of landmarks forms a shape. Shapes can be represented as vectors using the coordinates of the points in the shape. One shape is aligned to another with a similarity transform (allowing translation, scaling, and rotation) that minimizes the average Euclidean distance between shape points. The mean shape is the mean of the aligned training shapes.

In some embodiments, a search for landmarks from the mean shape aligned to the position and size of the face determined by a global face detector is started. Such a search then repeats the steps of suggesting a tentative shape by adjusting the locations of shape points by template matching of the image texture around each point and then conforming the tentative shape to a global shape model until convergence occurs. In some systems, individual template matches are unreliable and the shape model pools the results of the weak template matchers to form a stronger overall classifier. The entire search is repeated at each level in an image pyramid, from coarse to fine resolution.

Embodiments of a transformation system can capture an image or video stream on a client device and perform complex image manipulations locally on a client device such as client device 102 while maintaining a suitable user experience, computation time, and power consumption. The complex image manipulations may include size and shape changes, emotion transfers (e.g., changing a face from a frown to a smile), state transfers (e.g., aging a subject, reducing apparent age, changing gender), style transfers, graphical element application, and any other suitable image or video manipulation implemented by a convolutional neural network that has been configured to execute efficiently on a client device.

In some example embodiments, a computer animation model to transform image data can be used by a system where a user may capture an image or video stream of the user (e.g., a selfie) using a client device 102 having a neural network operating as part of a messaging client application 104 operating on the client device 102. The transform system operating within the messaging client application 104 determines the presence of a face within the image or video stream and provides modification icons associated with a computer animation model to transform image data, or the computer animation model can be present as associated with an interface described herein. The modification icons include changes which may be the basis for modifying the user's face within the image or video stream as part of the modification operation. Once a modification icon is selected, the transform system initiates a process to convert the image of the user to reflect the selected modification icon (e.g., generate a smiling face on the user). In some embodiments, a modified image or video stream may be presented in a graphical user interface displayed on the mobile client device as soon as the image or video stream is captured and a specified modification is selected. The transform system may implement a complex convolutional neural network on a portion of the image or video stream to generate and apply the selected modification. That is, the user may capture the image or video stream and be presented with a modified result in real time or near real time once a modification icon has been selected. Further, the modification may be persistent while the video stream is being captured and the selected modification icon remains toggled. Machine taught neural networks may be used to enable such modifications.

In some embodiments, the graphical user interface, presenting the modification performed by the transform system, may supply the user with additional interaction options. Such options may be based on the interface used to initiate the content capture and selection of a particular computer animation model (e.g. initiation from a content creator user interface). In various embodiments, a modification may be persistent after an initial selection of a modification icon. The user may toggle the modification on or off by tapping or otherwise selecting the face being modified by the transformation system. and store it for later viewing or browse to other areas of the imaging application. Where multiple faces are modified by the transformation system, the user may toggle the modification on or off globally by tapping or selecting a single face modified and displayed within a graphical user interface. In some embodiments, individual faces, among a group of multiple faces, may be individually modified or such modifications may be individually toggled by tapping or selecting the individual face or a series of individual faces displayed within the graphical user interface.

In some example embodiments, a graphical processing pipeline architecture is provided that enables different media overlays to be applied in corresponding different layers. Such a graphical processing pipeline provides an extensible rendering engine for providing multiple augmented reality content generators that are included in a composite media (e.g., image or video) or composite AR content for rendering by the messaging client application 104 (or the messaging system 100).

As discussed herein, the subject infrastructure supports the creation and sharing of interactive messages with interactive effects throughout various components of the messaging system 100. In an example, to provide such interactive effects, a given interactive message may include image data along with 2D data, or 3D data. The infrastructure as described herein enables other forms of 3D and interactive media (e.g., 2D media content) to be provided across the subject system, which allows for such interactive media to be shared across the messaging system 100 and alongside photo and video messages. In example embodiments described herein, messages can enter the system from a live camera or via from storage (e.g., where messages with 2D or 3D content or augmented reality (AR) effects (e.g., 3D effects, or other interactive effects are stored in memory or a database). In an example of an interactive message with 3D data, the subject system supports motion sensor input and manages the sending and storage of 3D data, and loading of external effects and asset data.

As mentioned above, an interactive message includes an image in combination with a 2D effect, or a 3D effect and depth data. In an example embodiment, a message is rendered using the subject system to visualize the spatial detail/geometry of what the camera sees, in addition to a traditional image texture. When a viewer interacts with this message by moving a client device, the movement triggers corresponding changes in the perspective the image and geometry are rendered at to the viewer.

In an embodiment, the subject system provides AR effects (which may include 3D effects using 3D data, or interactive 2D effects that do not use 3D data) that work in conjunction with other components of the system to provide particles, shaders, 2D assets and 3D geometry that can inhabit different 3D-planes within messages. The AR effects as described herein, in an example, are rendered in a real-time manner for the user.

As mentioned herein, a gyro-based interaction refers to a type of interaction in which a given client device's rotation is used as an input to change an aspect of the effect (e.g., rotating phone along x-axis in order to change the color of a light in the scene).

As mentioned herein, an augmented reality content generator refers to a real-time special effect and/or sound that may be added to a message and modifies image and/or 3D data with an AR effects and/other 3D content such as 3D animated graphical elements, 3D objects (e.g., non-animated), and the like.

The following discussion relates to example data that is stored in connection with such a message in accordance to some embodiments.

Figure 6:
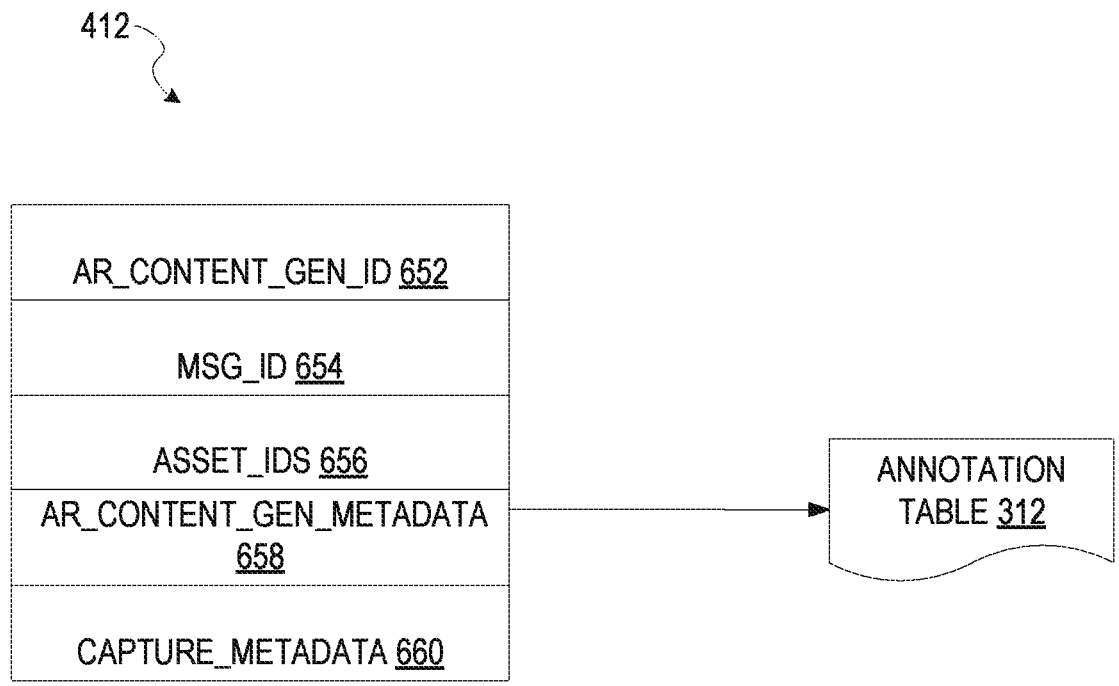
FIG. 6 is a schematic diagram illustrating a structure of the message annotations, as described in FIG. 4, including additional information corresponding to a given message, according to some embodiments.

FIG. 6 is a schematic diagram illustrating a structure of the message annotations 412, as described above in FIG. 4, including additional information corresponding to a given message, according to some embodiments, generated by the messaging client application 104 or the eyewear system 160.

Figure 7:
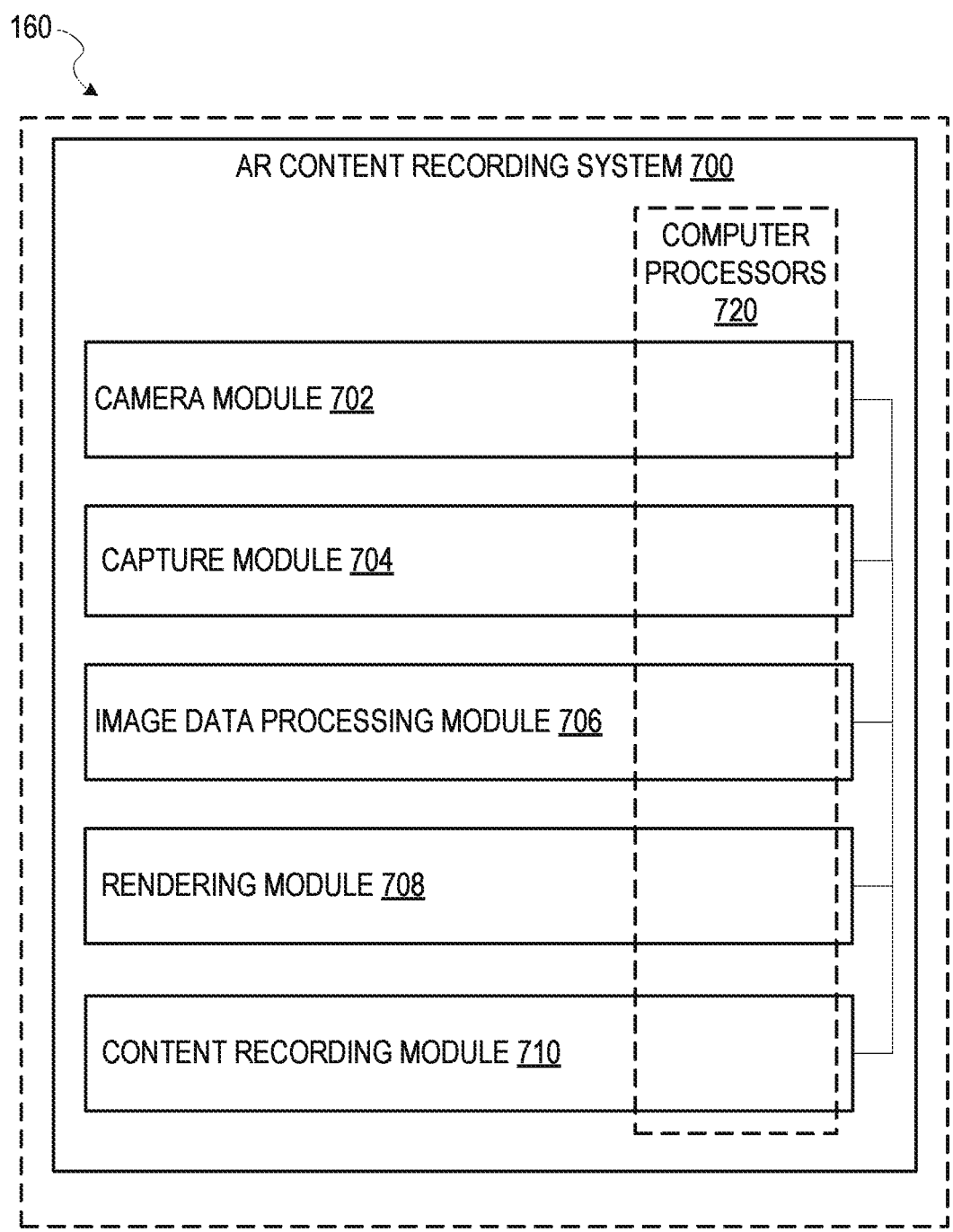
FIG. 7 is a block diagram illustrating various modules of an eyewear system, according to certain example embodiments.

In an embodiment, the content of a particular message 400, as shown in FIG. 3, including the additional data shown in FIG. 6 is used to populate the message table 314 stored within the database 120 for a given message, which is then accessible by the messaging client application 104. As illustrated in FIG. 6, message annotations 412 includes the following components corresponding to various data:
    augmented reality (AR) content identifier 652: identifier of an AR content generator utilized in the message
    message identifier 654: identifier of the message
    asset identifiers 656: a set of identifiers for assets in the message. For example, respective asset identifiers can be included for assets that are determined by the particular AR content generator. In an embodiment, such assets are created by the AR content generator on the sender side client device, uploaded to the messaging server application 114, and utilized on the receiver side client device in order to recreate the message. Examples of typical assets include:
    The original still RGB image(s) captured by the camera
    The post-processed image(s) with AR content generator effects applied to the original image
    augmented reality (AR) content metadata 658: additional metadata associated with the AR content generator corresponding to the AR identifier 652, such as:
    AR content generator category: corresponding to a type or classification for a particular AR content generator
    AR content generator carousel index
    carousel group: This can be populated and utilized when eligible post-capture AR content generators are inserted into a carousel interface. In an implementation, a new value "AR_DEFAULT_GROUP" (e.g., a default group assigned to an AR content generator can be added to the list of valid group names.

capture metadata 660 corresponding to additional metadata, such as:
  camera image metadata
    camera intrinsic data
      focal length
      principal point
    other camera information (e.g., camera position)
  sensor information
    gyroscopic sensor data
    position sensor data
    accelerometer sensor data
    other sensor data
    location sensor data FIG. 7 is a block diagram illustrating various modules of an eyewear system 160, according to certain example embodiments. The eyewear system 160 is shown as including an AR content recording system 700. As further shown, the AR content recording system 700 includes a camera module 702, a capture module 704, an image data processing module 706, a rendering module 708, and a content recording module 710. The various modules of the AR content recording system 700 are configured to communicate with each other (e.g., via a bus, shared memory, or a switch). Any one or more of these modules may be implemented using one or more computer processors 720 (e.g., by configuring such one or more computer processors to perform functions described for that module) and hence may include one or more of the computer processors 720 (e.g., a set of processors provided by the eyewear device 150).

Any one or more of the modules described may be implemented using hardware alone (e.g., one or more of the computer processors 720 of a machine (e.g., machine 1200) or a combination of hardware and software. For example, any described module of the eyewear system 160 may physically include an arrangement of one or more of the computer processors 720 (e.g., a subset of or among the one or more computer processors of the machine (e.g., machine 1200) configured to perform the operations described herein for that module. As another example, any module of the AR content recording system 700 may include software, hardware, or both, that configure an arrangement of one or more computer processors 720 (e.g., among the one or more computer processors of the machine (e.g., machine 1200) to perform the operations described herein for that module. Accordingly, different modules of the AR content recording system 700 may include and configure different arrangements of such computer processors 720 or a single arrangement of such computer processors 720 at different points in time. Moreover, any two or more modules of the eyewear system 160 may be combined into a single module, and the functions described herein for a single module may be subdivided among multiple modules. Furthermore, according to various example embodiments, modules described herein as being implemented within a single machine, database, or device may be distributed across multiple machines, databases, or devices.

The camera module 702 performs camera related operations, including functionality for operations involving one or more cameras of the eyewear device 150. In an example, camera module 702 can access camera functionality across different processes that are executing on the eyewear device 150, determining surfaces for face or surface tracking, responding to various requests (e.g., involving image data of a particular resolution or format) for camera data or image data (e.g., frames) from such processes, providing metadata to such processes that are consuming the requested camera data or image data. As mentioned herein, a "process" or "computing process" can refer to an instance of a computer program that is being executed by one or more threads of a given processor(s).

As mentioned herein, surface tracking refers to operations for tracking one or more representations of surfaces corresponding to planes (e.g., a given horizontal plane, a floor, a table) in the input frame. In an example, surface tracking is accomplished using hit testing and/or ray casting techniques. Hit testing, in an example, determines whether a selected point (e.g., pixel or set of pixels) in the input frame intersects with a surface or plane of a representation of a physical object in the input frame. Ray casting, in an example, utilizes a Cartesian based coordinate system (e.g., x and y coordinates) and projects a ray (e.g., vector) into the camera's view of the world, as captured in the input frame, to detect planes that the ray intersects.

As further illustrated, the camera module 702 receives the input frame (or alternatively a duplicate of the input frame in an embodiment). The camera module 702 can include various tracking functionality based on a type of object to track. In an example, the camera module 702 includes tracking capabilities for surface tracking, face tracking, object tracking, and the like. In an implementation, the camera module 702 may only execute one of each of a plurality of tracking processes at a time for facilitating the management of computing resources at the client device 102 or eyewear device 150. In addition, the camera module 702 may perform one or more object recognition or detection operations on the input frame.

As referred to herein, tracking refers to operations for determining spatial properties (e.g., position and/or orientation) of a given object (or portion thereof) during a post-processing stage. In an implementation, during tracking, the object's position and orientation are measured in a continuous manner. Different objects may be tracked, such as a user's head, eyes, or limbs, surfaces, or other objects. Tracking involves dynamic sensing and measuring to enable virtual objects and/or effects to be rendered with respect to physical objects in a three-dimensional space corresponding to a scene (e.g., the input frame). Thus, the camera module 702 determines metrics corresponding to at least the relative position and orientation of one or more physical objects in the input frame and includes these metrics in tracking data which is provided to the rendering module 708. In an example, the camera module 702 updates (e.g., track over time) such metrics from frame to subsequent frame.

In an implementation, the camera module 702 provides, as output, tracking data (e.g., metadata) corresponding to the aforementioned metrics (e.g., position and orientation). In some instances, the camera module 702 includes logic for shape recognition, edge detection, or any other suitable object detection mechanism. The object of interest may also be determined by the camera module 702 to be an example of a predetermined object type, matching shapes, edges, or landmarks within a range to an object type of a set of predetermined object types.

In an implementation, the camera module 702 can utilize techniques which combines information from the device's motion sensors (e.g., accelerometer and gyroscope sensors, and the like) with an analysis of the scene provided in the input frame. For example, the camera module 702 detects features in the input frame, and as a result, tracks differences in respective positions of such features across several input frames using information derived at least in part on data from the motion sensors of the device.

As mentioned herein, face tracking refers to operations for tracking representations of facial features, such as portions of a user's face, in the input frame. In some embodiments, the camera module 702 includes facial tracking logic to identify all or a portion of a face within the one or more images and track landmarks of the face across the set of images of the video stream. As mentioned herein, object tracking refers to tracking a representation of a physical object in the input frame.

In an embodiment, the camera module 702 determines a gaze direction of a user wearing the eyewear device, and facilitates the generation of AR content based on the determined gaze direction. Examples of this are discussed in further detail in FIG. 8A, FIG. 8B, and FIG. 9 below.

In an embodiment, the camera module 702 acts as an intermediary between other components of the AR content recording system 700 and the capture module 704. As mentioned above, the camera module 702 can receive requests for captured image data from the image data processing module 706. The camera module 702 can also receive requests for the captured image data from the content recording module 710. The camera module 702 can forward such requests to the capture module 704 for processing.

The capture module 704 captures images (which may also include depth data) captured by one or more cameras of eyewear device 150 (e.g., in response to the aforementioned requests from other components). For example, an image is a photograph captured by an optical sensor (e.g., camera) of the eyewear device 150. An image includes one or more real-world features, such as a user's face or real-world object(s) detected in the image. In some embodiments, an image includes metadata describing the image. Each captured image can be included in a data structure mentioned herein as a "frame", which can include the raw image data along with metadata and other information. In an embodiment, capture module 704 can send captured image data and metadata as (captured) frames to one or more components of the AR content recording system 700. The sending of the captured frames can occur asynchronously, which may cause synchronization issues as one component might receive and process a given frame slightly before or after another component receives and processes the same frame. In applications for rendering AR effects and AR environments, such synchronization issues can result in a perceived lag from the viewpoint of the user (e.g., a glitch or perception of non-responsiveness), which reduces and detracts from the immersive experience of the AR environments. As discussed further below, embodiments of the subject technology therefore enables generating time information for each captured frame (e.g., timestamps) to facilitate synchronization of operations and improve rendering of AR effects and AR environments which a presented to the viewing user of the eyewear device 150.

The image data processing module 706 generates tracking data and other metadata for captured image data, including metadata associated with operations for generating AR content and AR effects applied to the captured image data. The image data processing module 706 performs operations on the received image data. For example, various image processing operations are performed by the image data processing module 706. The image data processing module 706 performs various operations based on algorithms or techniques that correspond to animations and/or providing visual and/or auditory effects to the received image data. In an embodiment, a given augmented reality content generator can utilize the image data processing module 706 to perform operations as part of generating AR content and AR effects which is then provided to a rendering process to render such AR content and AR effects (e.g., including 2D effects or 3D effects) and the like.

The rendering module 708 performs rendering of AR content for display by the eyewear system 160 based on data provided by at least one of the aforementioned modules. In an example, the rendering module 708 utilizes a graphical processing pipeline to perform graphical operations to render the AR content for display. The rendering module 708 implements, in an example, an extensible rendering engine which supports multiple image processing operations corresponding to respective augmented reality content generators. In an example, the rendering module 708 can receive a composite AR content item for rendering on a display provided by eyewear device 150.

In some implementations, the rendering module 708 provide a graphics system that renders two-dimensional (2D) objects or objects from a three-dimensional (3D) world (real or imaginary) onto a 2D display screen. Such a graphics system (e.g., one included on the eyewear device 150) includes a graphics processing unit (GPU) in some implementations for performing image processing operations and rendering graphical elements for display.

In an implementation, the GPU includes a logical graphical processing pipeline, which can receive a representation of a 2D or 3D scene and provide an output of a bitmap that represents a 2D image for display. Existing application programming interfaces (APIs) have implemented graphical pipeline models. Examples of such APIs include the Open Graphics Library (OPENGL) API and the METAL API. The graphical processing pipeline includes a number of stages to convert a group of vertices, textures, buffers, and state information into an image frame on the screen. In an implementation, one of the stages of the graphical processing pipeline is a shader, which may be utilized as part of a particular augmented reality content generator that is applied to an input frame (e.g., image or video). A shader can be implemented as code running on a specialized processing unit, also referred to as a shader unit or shader processor, usually executing several computing threads, programmed to generate appropriate levels of color and/or special effects to fragments being rendered. For example, a vertex shader processes attributes (position, texture coordinates, color, etc.) of a vertex, and a pixel shader processes attributes (texture values, color, z-depth and alpha value) of a pixel. In some instances, a pixel shader is referred to as a fragment shader.

It is to be appreciated that other types of shader processes may be provided. In an example, a particular sampling rate is utilized, within the graphical processing pipeline, for rendering an entire frame, and/or pixel shading is performed at a particular per-pixel rate. In this manner, a given electronic device (e.g., the eyewear device 150) operates the graphical processing pipeline to convert information corresponding to objects into a bitmap that can be displayed by the electronic device.

The content recording module 710 sends a request(s) to the camera module 702 to initiate recording of image data by one or more cameras provided by the eyewear device 150. In an embodiment, the camera module 702 acts as intermediary between other components in the AR content recording system. For example, the camera module can receive a request from the content recording module 710 to initiate recording, and forward the request to the capture module 704 for processing. The capture module 704, upon receiving the request from the camera module 702, performs operations to initiate image data capture by the camera(s) provided by the eyewear device 150. Captured image data, including timestamp information for each frame from the captured image data, can then be sent to the content recording module 710 for processing. In an example, the content recording module 710 can perform operations to process captured image data for rendering by the rendering module 708.

In an embodiment, components of the AR content recording system 700 can communicate using an inter-process communication (IPC) protocol, In an embodiment, components of the AR content recording system 700 can communicate through an API provided by the AR content recording system 700.

In an embodiment, the camera module 702 receives a signal or command (or a request) to stop recording of image data (e.g., sent from the content recording module 710). In response, the camera module 702 sends a request to the capture module 704 to stop capturing image data. The capture module 704, in response to the request to stop recording, complies with the request and ceases further operations to capture image data using one or more cameras of the eyewear device 150. The camera module 702, after receiving the signal or command to stop recording, can also asynchronously send a signal to the image data processing module 706 that recording of image data (e.g., capture of image data by the capture module 704) has (requested to be) stopped. The image data processing module 706, after receiving the signal, performs operations to complete or finish image processing operations, including performing operations to generate metadata related to AR content items and AR effects. Such metadata can then be sent to the capture module 704, which then generates a composite AR content item, including the metadata. The composite AR content item can be received by the rendering module 708 and rendered for display on a display device provided by the eyewear device 150.

Figure 8B:
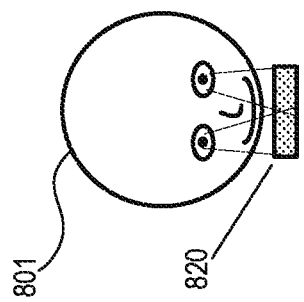
FIGS. 8A and 8B illustrate examples of tracking a gaze direction to perform an operation(s) by the eyewear system in accordance with implementations of the subject technology.
Figure 8A:
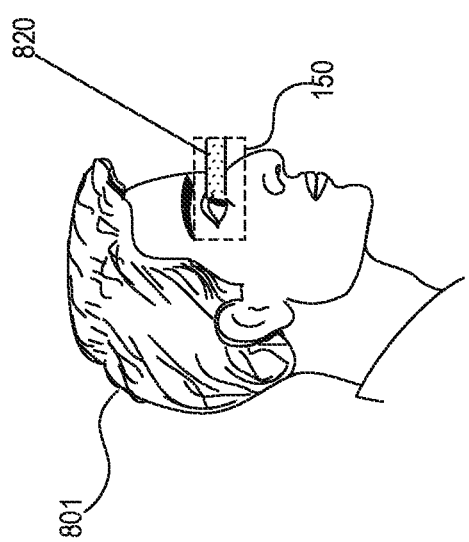

FIGS. 8A and 8B illustrate examples of tracking a gaze direction to perform an augmented reality operation(s) in accordance with implementations of the subject technology. The following discussion relates to components of the eyewear device 150, which includes various cameras to enable tracking a gaze direction of eyes of a user's face.

As shown in FIG. 8A, images are captured and analyzed at least one camera of the eyewear device 150 to determine the relative positions of eyes of user 801 within a field of view 820. In an implementation, the eyewear device 150 can differentiate the user's pupils, and can utilize the relative position of the pupils with respect to the eye position to determine a gaze direction. For example, in FIG. 8B, the eyewear device 150 can use the detected position of the user's pupils relative to the user's eyes, and determine an area on the display of the eyewear device 150 at which the user 801 is looking within a field of view 820. Additionally, in an implementation, the eyewear device 150 can also detect movements such as a user closing his or her eyes for a particular period of time, which may be used to initiate one or more operations by the eyewear system 160.

In an embodiment, to determine a gaze direction of a user, the camera module 702 determine a relative position of the user relative to the eyewear device 150, as well as dimensions or other aspects of the user at that position, which includes determining relative positions of the user's head and the user's eyes. In an example, the camera module 702 can differentiate the user's pupils, the system can also utilize the relative position of the pupils with respect to the eye position. In an example, the user is looking left (e.g., to the user's right), the camera module 702 determines that a center point of each user's pupil is to the left (e.g., in image data) of the center point of the respective eye. In an example where the user is looking "down", the camera module 702 determines that positions of the pupils have moved below a center point of the eyes. In an example where the user is looking "up", the camera module 702 determines that positions of the pupils have moved above a center point of the eyes. The position of the pupils can change without the user moving his or her head, and in an example, the camera module 702 can therefore detect a gaze direction without a change in the user's head position. The eyewear system 160 can generate AR content based on the detected position of the user's pupils relative to the user's eyes, and the eyewear system 160 can render the AR content in a determined area on the display of the eyewear device 150 at which the user is currently looking.

Figure 9:
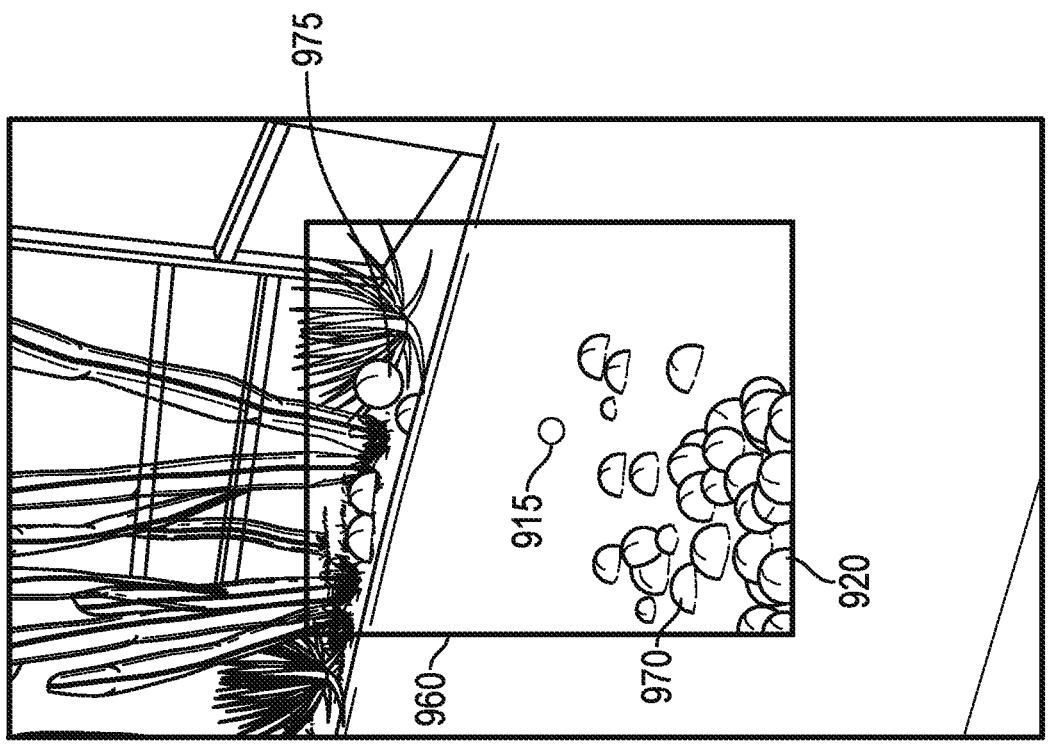
FIG. 9 illustrates examples of AR content generated in a field of view of a user based on a determined gaze direction of the user while using the eyewear device.
Figure 9:
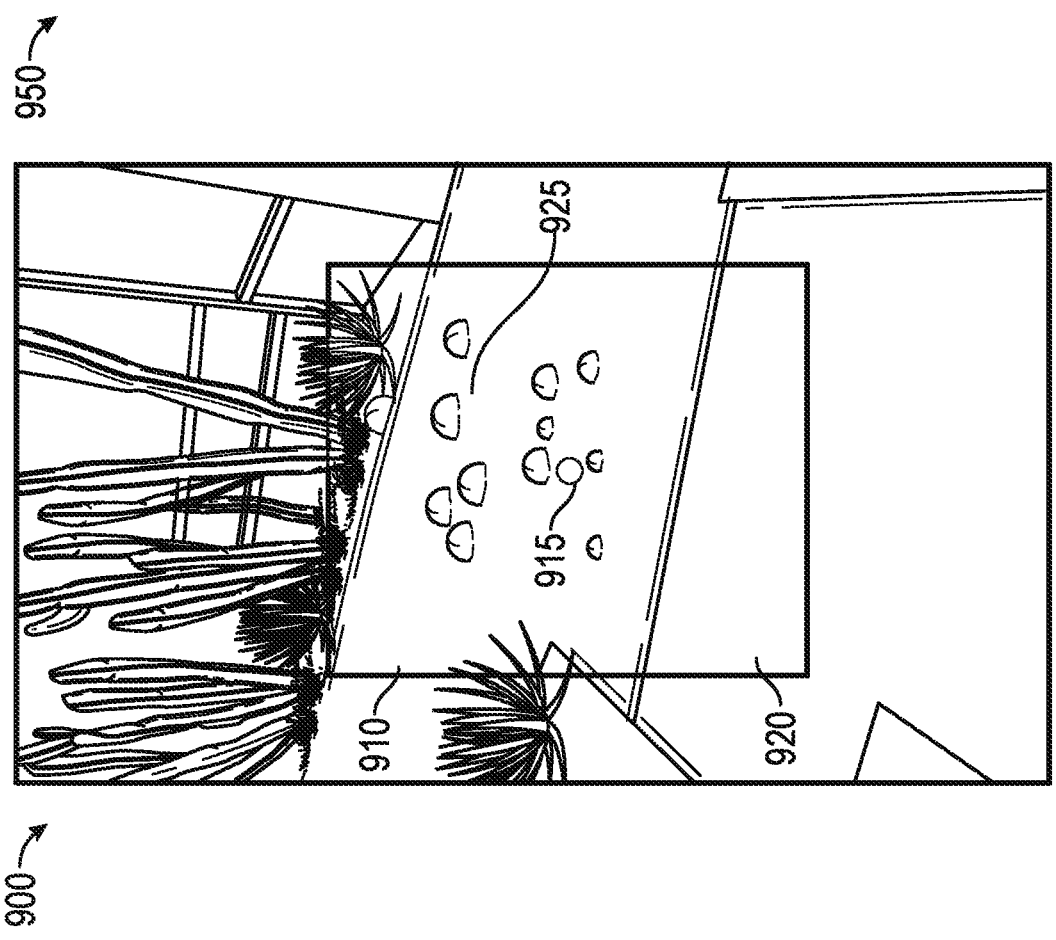

FIG. 9 illustrates examples of AR content generated in a field of view of a user based on a determined gaze direction of the user while using the eyewear device 150.

As shown in a first AR environment 900, a field of view 910 includes an anchor point 915 based on a determined gaze direction of a user. A surface 920 corresponding to a ground plane in the field of view 910 is identified. In an embodiment, a distance between the surface 920 and the anchor point 915 is determined. Based on the distance, AR content 925 (e.g., virtual AR snowballs) is generated and rendered for display by the eyewear system 160.

As shown in a second AR environment 950, a field of view 960 includes the anchor point 915 based on the determined gaze direction of the user. AR content 970, representing a set of AR content items (e.g., virtual AR snowballs), has been generated and rendered in the field of view 960 based at least in part on a determined distance between the anchor point 915 and the identified surface 920. As further shown, AR content 975 has also been generated and rendered for display by the eyewear system 160, which in this example, will be animated to fall into position on top of the AR content 970.

Figure 10:
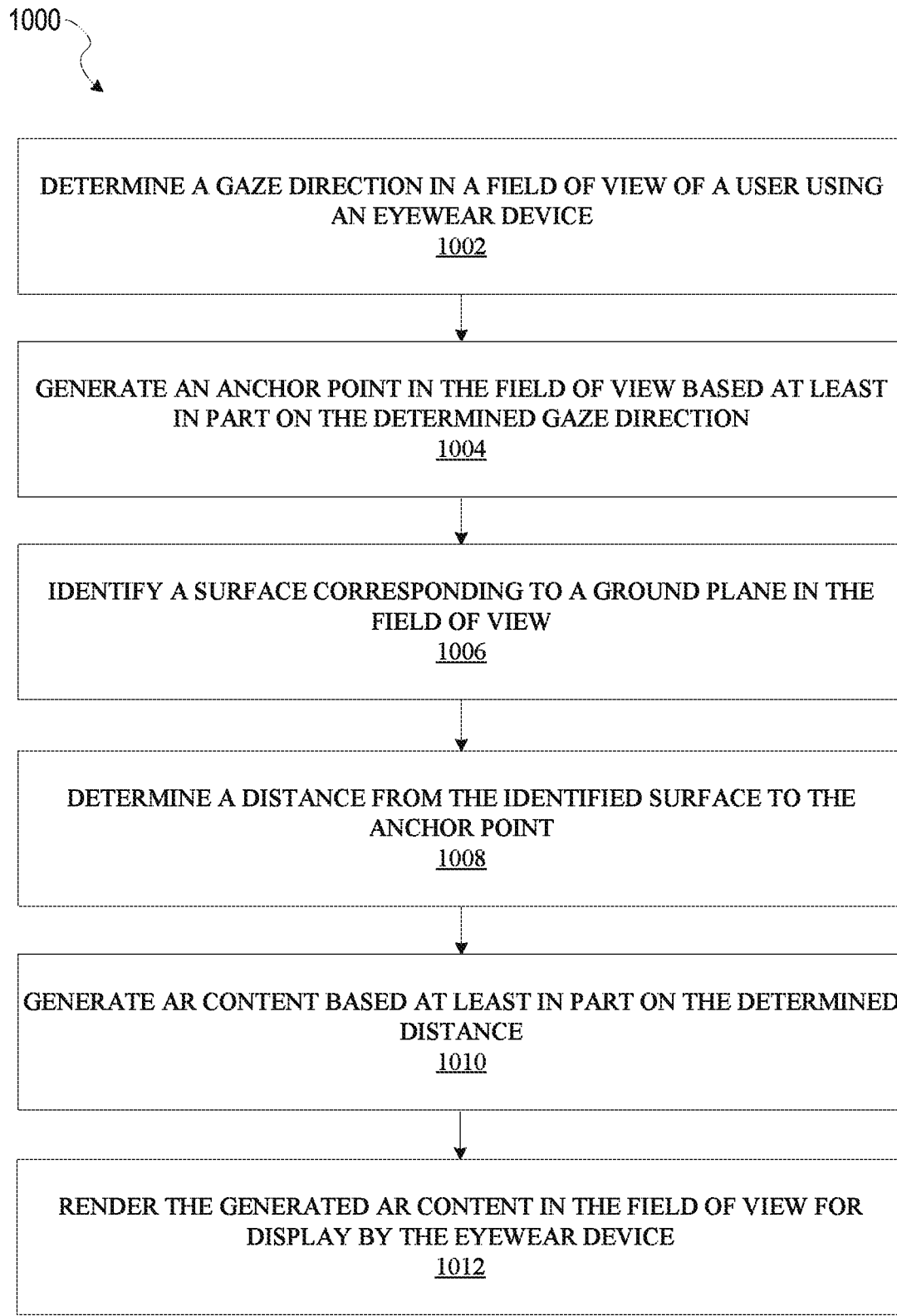
FIG. 10 is a flowchart illustrating a method, according to certain example embodiments.

FIG. 10 is a flowchart illustrating a method 1000, according to certain example embodiments. The method 1000 may be embodied in computer-readable instructions for execution by one or more computer processors such that the operations of the method 1000 may be performed in part or in whole by the eyewear device 150, particularly with respect to respective components of the AR content recording system 700 described above in FIG. 7; accordingly, the method 1000 is described below by way of example with reference thereto. However, it shall be appreciated that at least some of the operations of the method 1000 may be deployed on various other hardware configurations and the method 1000 is not intended to be limited to the AR content recording system 700.

At operation 1002, the camera module 702 determines a gaze direction in a field of view of a user using an eyewear device (e.g., the eyewear device 150).

At operation 1004, the camera module 702 generates an anchor point in the field of view based at least in part on the determined gaze direction.

At operation 1006, the camera module 702 identifies a surface corresponding to a ground plane in the field of view.

At operation 1008, the camera module 702 determines a distance from the identified surface to the anchor point.

At operation 1010, the image data processing module 706 generates AR content based at least in part on the determined distance.

At operation 1012, the rendering module 708 renders the generated AR content in the field of view for display by the eyewear device (e.g., the eyewear device 150).

In embodiments, the camera module 702 generates the anchor point which comprises performing a ray casting operation, based at least in part on the gaze direction, to select a point in the field of view, the point corresponding to the anchor point.

In embodiments, the ray casting operation comprises: determining a location of a pupil or iris of the user, projecting a ray, from the location of the pupil or iris, in a direction toward the field of view, the field of view comprising a set of pixels, determining at least one pixel from the field of view that intersects the ray, and selecting the at least one pixel as the anchor point.

The camera module 702 determines the gaze direction is based on a head orientation and a relative position of a pupil or iris of the user using the eyewear device.

In embodiments, the camera module 702 identifies the surface corresponding to the ground plane is based on a surface detection process.

In embodiments, the surface detection process comprises generating a point cloud based on the field of view, the point cloud comprising a set of feature points, each feature point include a set of respective x, y, and z coordinates in a three-dimensional space, and performing hit testing on the point cloud to determine a first surface plane in the field of view, the hit testing determining an intersection of at least one feature point corresponding to the first surface plane below a median feature point in the point cloud.

In embodiments, the camera module 702 performs hit testing that comprises generating a three-dimensional line that includes a starting position corresponding to a position of a pupil or iris of the user and extends from the gaze direction to the one feature point corresponding to the first surface plane in the field of view.

In embodiments, the camera module 702 determines the distance from the identified surface to the anchor point which comprises generating a second anchor point within the identified surface, determining a first distance between the second anchor point and the anchor point in the field of view, the second anchor point being at a position below relative to the anchor point, and selecting a particular position along the first distance between the second anchor point and the anchor point.

In embodiments, the image data processing module 706 renders the generated augmented reality content in the field of view for display by the eyewear device which comprises generating a first three-dimensional object, rendering the first three-dimensional object at the particular position, generating a second three-dimensional object, and rendering the second three-dimensional object at a second position above or below the first three-dimensional object.

In embodiments, the first three-dimensional object is different type of object than the second three-dimensional object, or the first three-dimensional object is a same type of object as the second three-dimensional object.

Figure 11:
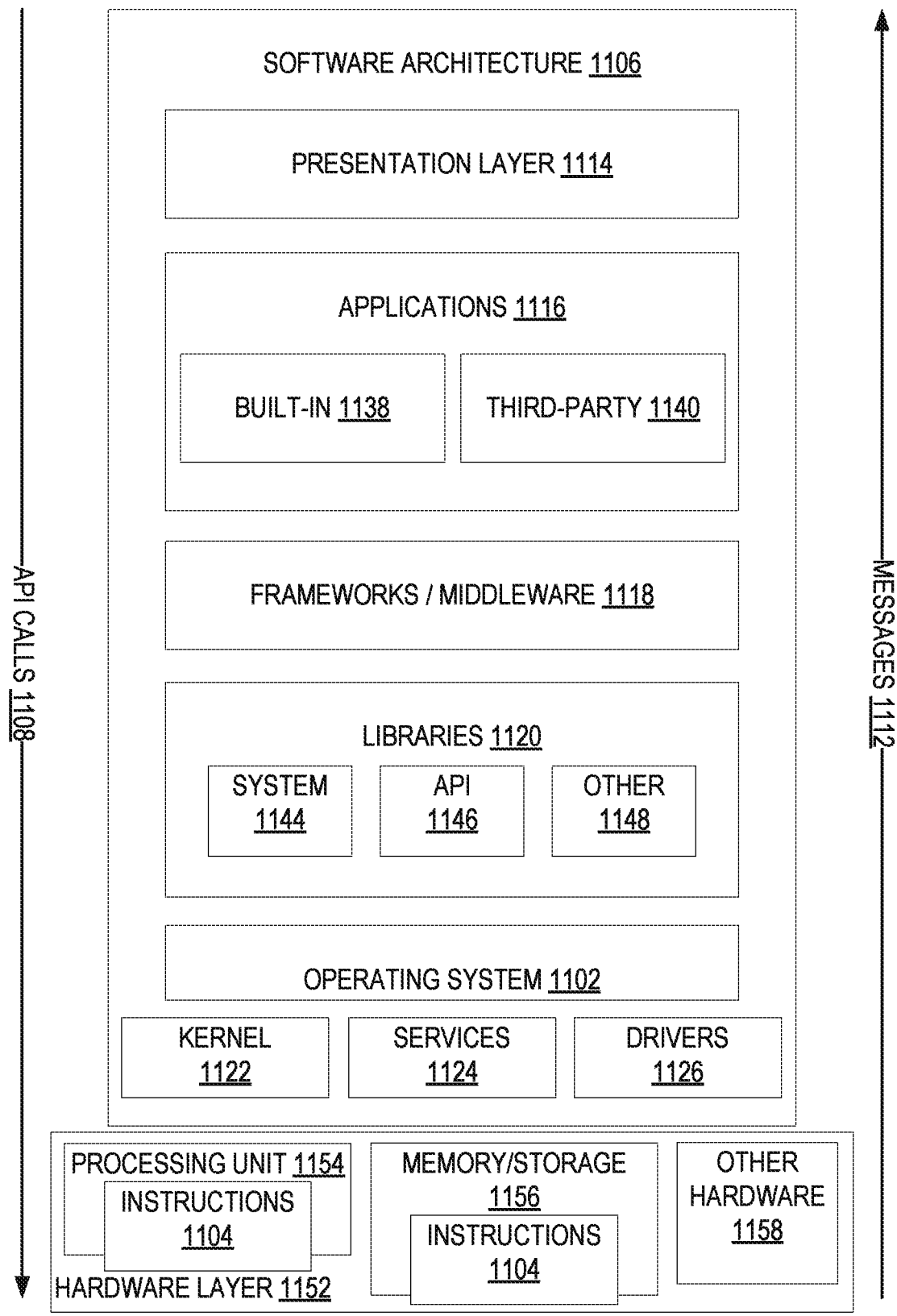
FIG. 11 is block diagram showing a software architecture within which the present disclosure may be implemented, in accordance with some example embodiments.

FIG. 11 is a block diagram illustrating an example software architecture 1106, which may be used in conjunction with various hardware architectures herein described. FIG. 11 is a non-limiting example of a software architecture and it will be appreciated that many other architectures may be implemented to facilitate the functionality described herein. The software architecture 1106 may execute on hardware such as machine 1200 of FIG. 12 that includes, among other things, processors 1204, memory 1214, and (input/output) I/O components 1218. A representative hardware layer 1152 is illustrated and can represent, for example, the machine 1200 of FIG. 12. The representative hardware layer 1152 includes a processing unit 1154 having associated executable instructions 1104. Executable instructions 1104 represent the executable instructions of the software architecture 1106, including implementation of the methods, components, and so forth described herein. The hardware layer 1152 also includes memory and/or storage modules memory/storage 1156, which also have executable instructions 1104. The hardware layer 1152 may also comprise other hardware 1158.

In the example architecture of FIG. 11, the software architecture 1106 may be conceptualized as a stack of layers where each layer provides particular functionality. For example, the software architecture 1106 may include layers such as an operating system 1102, libraries 1120, frameworks/middleware 1118, applications 1116, and a presentation layer 1114. Operationally, the applications 1116 and/or other components within the layers may invoke API calls 1108 through the software stack and receive a response as in messages 1112 to the API calls 1108. The layers illustrated are representative in nature and not all software architectures have all layers. For example, some mobile or special purpose operating systems may not provide a frameworks/middleware 1118, while others may provide such a layer. Other software architectures may include additional or different layers.

The operating system 1102 may manage hardware resources and provide common services. The operating system 1102 may include, for example, a kernel 1122, services 1124, and drivers 1126. The kernel 1122 may act as an abstraction layer between the hardware and the other software layers. For example, the kernel 1122 may be responsible for memory management, processor management (e.g., scheduling), component management, networking, security settings, and so on. The services 1124 may provide other common services for the other software layers. The drivers 1126 are responsible for controlling or interfacing with the underlying hardware. For instance, the drivers 1126 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 1120 provide a common infrastructure that is used by the applications 1116 and/or other components and/or layers. The libraries 1120 provide functionality that allows other software components to perform tasks in an easier fashion than to interface directly with the underlying operating system 1102 functionality (e.g., kernel 1122, services 1124 and/or drivers 1126). The libraries 1120 may include system libraries 1144 (e.g., C standard library) that may provide functions such as memory allocation functions, string manipulation functions, mathematical functions, and the like. In addition, the libraries 1120 may include API libraries 1146 such as media libraries (e.g., libraries to support presentation and manipulation of various media format such as MPREG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 1120 may also include a wide variety of other libraries 1148 to provide many other APIs to the applications 1116 and other software components/modules.

The frameworks/middleware 1118 (also sometimes referred to as middleware) provide a higher-level common infrastructure that may be used by the applications 1116 and/or other software components/modules. For example, the frameworks/middleware 1118 may provide various graphic user interface (GUI) functions, high-level resource management, high-level location services, and so forth. The frameworks/middleware 1118 may provide a broad spectrum of other APIs that may be used by the applications 1116 and/or other software components/modules, some of which may be specific to a particular operating system 1102 or platform.

The applications 1116 include built-in applications 1138 and/or third-party applications 1140. Examples of representative built-in applications 1138 may include, but are not limited to, a contacts application, a browser application, a book reader application, a location application, a media application, a messaging application, and/or a game application. Third-party applications 1140 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 1140 may invoke the API calls 1108 provided by the mobile operating system (such as operating system 1102) to facilitate functionality described herein.

The applications 1116 may use built in operating system functions (e.g., kernel 1122, services 1124 and/or drivers 1126), libraries 1120, and frameworks/middleware 1118 to create user interfaces to interact with users of the system. Alternatively, or additionally, in some systems interactions with a user may occur through a presentation layer, such as presentation layer 1114. In these systems, the application/component 'logic' can be separated from the aspects of the application/component that interact with a user.

Figure 12:
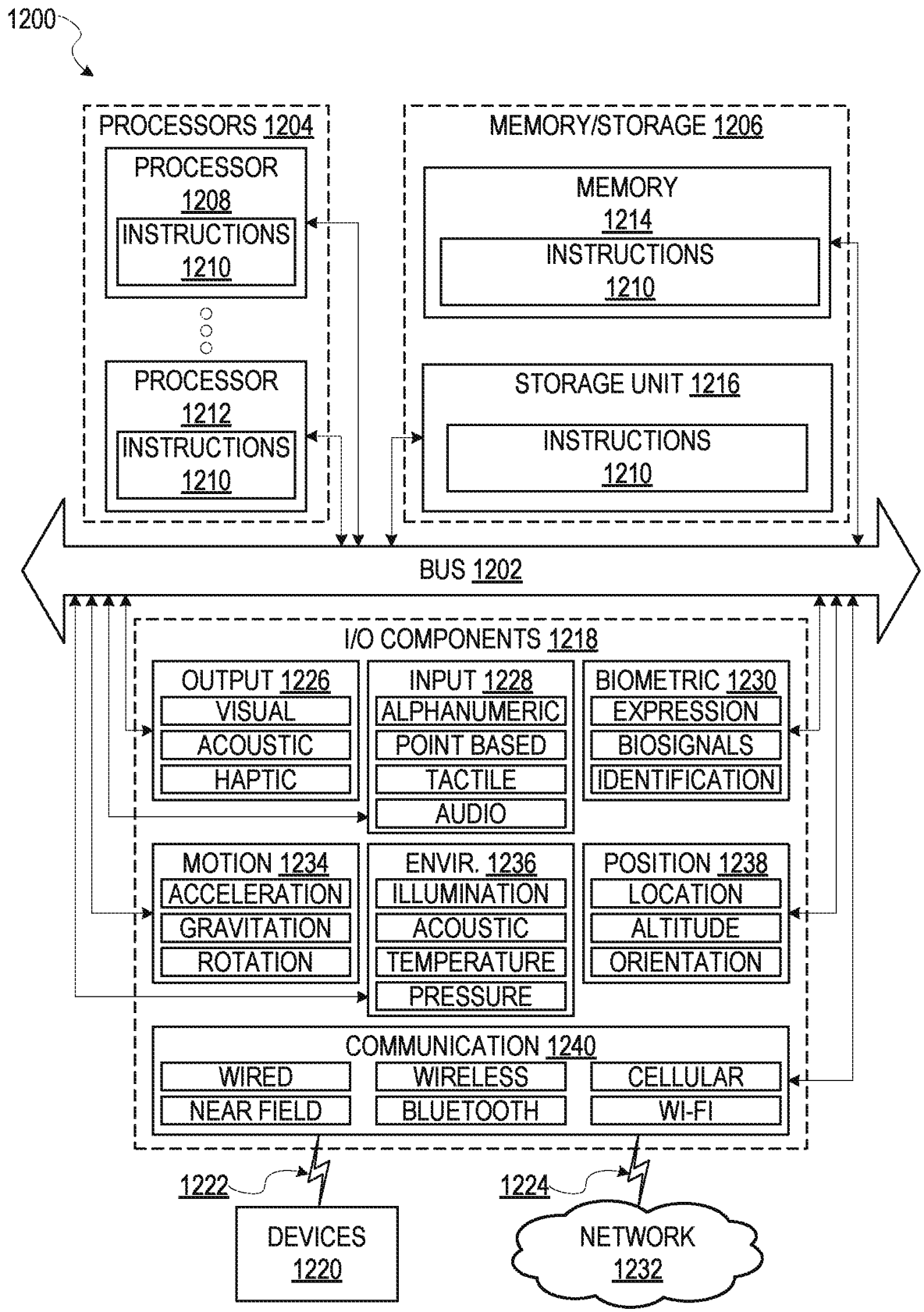
FIG. 12 is a diagrammatic representation of a machine, in the form of a computer system within which a set of instructions may be executed for causing the machine to perform any one or more of the methodologies discussed, in accordance with some example embodiments.

FIG. 12 is a block diagram illustrating components of a machine 1200, according to some example embodiments, able to read instructions from a machine-readable medium (e.g., a machine-readable storage medium) and perform any one or more of the methodologies discussed herein. Specifically, FIG. 12 shows a diagrammatic representation of the machine 1200 in the example form of a computer system, within which instructions 1210 (e.g., software, a program, an application, an applet, an app, or other executable code) for causing the machine 1200 to perform any one or more of the methodologies discussed herein may be executed. As such, the instructions 1210 may be used to implement modules or components described herein. The instructions 1210 transform the general, non-programmed machine 1200 into a particular machine 1200 programmed to carry out the described and illustrated functions in the manner described. In alternative embodiments, the machine 1200 operates as a standalone device or may be coupled (e.g., networked) to other machines. In a networked deployment, the machine 1200 may operate in the capacity of a server machine or a client machine in a server-client network environment, or as a peer machine in a peer-to-peer (or distributed) network environment. The machine 1200 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1210, sequentially or otherwise, that specify actions to be taken by machine 1200. Further, while only a single machine 1200 is illustrated, the term 'machine' shall also be taken to include a collection of machines that individually or jointly execute the instructions 1210 to perform any one or more of the methodologies discussed herein.

The machine 1200 may include processors 1204, including processor 1208 to processor 1212, memory/storage 1206, and I/O components 1218, which may be configured to communicate with each other such as via a bus 1202. The memory/storage 1206 may include a memory 1214, such as a main memory, or other memory storage, and a storage unit 1216, both accessible to the processors 1204 such as via the bus 1202. The storage unit 1216 and memory 1214 store the instructions 1210 embodying any one or more of the methodologies or functions described herein. The instructions 1210 may also reside, completely or partially, within the memory 1214, within the storage unit 1216, within at least one of the processors 1204 (e.g., within the processor's cache memory), or any suitable combination thereof, during execution thereof by the machine 1200. Accordingly, the memory 1214, the storage unit 1216, and the memory of processors 1204 are examples of machine-readable media.

The I/O components 1218 may include a wide variety of components to receive input, provide output, produce output, transmit information, exchange information, capture measurements, and so on. The specific I/O components 1218 that are included in a particular machine 1200 will depend on the type of machine. For example, portable machines such as mobile phones will likely include a touch input device or other such input mechanisms, while a headless server machine will likely not include such a touch input device. It will be appreciated that the I/O components 1218 may include many other components that are not shown in FIG. 12. The I/O components 1218 are grouped according to functionality merely for simplifying the following discussion and the grouping is in no way limiting. In various example embodiments, the I/O components 1218 may include output components 1226 and input components 1228. The output components 1226 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1228 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 1218 may include biometric components 1230, motion components 1234, environmental components 1236, or position components 1238 among a wide array of other components. For example, the biometric components 1230 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 1234 may include acceleration sensor components (e.g., accelerometer), gravitation sensor components, rotation sensor components (e.g., gyroscope), and so forth. The environmental components 1236 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1238 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1218 may include communication components 1240 operable to couple the machine 1200 to a network 1232 or devices 1220 via coupling 1224 and coupling 1222, respectively. For example, the communication components 1240 may include a network interface component or other suitable device to interface with the network 1232. In further examples, communication components 1240 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1220 may be another machine or any of a wide variety of peripheral devices (e.g., a peripheral device coupled via a USB).

Moreover, the communication components 1240 may detect identifiers or include components operable to detect identifiers. For example, the communication components 1240 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1240, such as, location via Internet Protocol (IP) geo-location, location via Wi-Fi® signal triangulation, location via detecting a NFC beacon signal that may indicate a particular location, and so forth.

The following discussion relates to various terms or phrases that are mentioned throughout the subject disclosure.

'Signal Medium' refers to any intangible medium that is capable of storing, encoding, or carrying the instructions for execution by a machine and includes digital or analog communications signals or other intangible media to facilitate communication of software or data. The term 'signal medium' shall be taken to include any form of a modulated data signal, carrier wave, and so forth. The term 'modulated data signal' means a signal that has one or more of its characteristics set or changed in such a matter as to encode information in the signal. The terms 'transmission medium' and 'signal medium' mean the same thing and may be used interchangeably in this disclosure.

'Communication Network' refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other types of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long-range protocols, or other data transfer technology.

'Processor' refers to any circuit or virtual circuit (a physical circuit emulated by logic executing on an actual processor) that manipulates data values according to control signals (e.g., 'commands', 'op codes', 'machine code', etc.) and which produces corresponding output signals that are applied to operate a machine. A processor may, for example, be a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC) or any combination thereof. A processor may further be a multi-core processor having two or more independent processors (sometimes referred to as 'cores') that may execute instructions contemporaneously.

'Machine-Storage Medium' refers to a single or multiple storage devices and/or media (e.g., a centralized or distributed database, and/or associated caches and servers) that store executable instructions, routines and/or data. The term shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks The terms 'machine-storage medium,' 'device-storage medium,' 'computer-storage medium' mean the same thing and may be used interchangeably in this disclosure. The terms 'machine-storage media,' 'computer-storage media,' and 'device-storage media' specifically exclude carrier waves, modulated data signals, and other such media, at least some of which are covered under the term 'signal medium.'

'Component' refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A 'hardware component' is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software), may be driven by cost and time considerations. Accordingly, the phrase 'hardware component'(or 'hardware-implemented component') should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, 'processor-implemented component' refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a 'cloud computing' environment or as a 'software as a service' (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

'Carrier Signal' refers to any intangible medium that is capable of storing, encoding, or carrying instructions for execution by the machine, and includes digital or analog communications signals or other intangible media to facilitate communication of such instructions. Instructions may be transmitted or received over a network using a transmission medium via a network interface device.

'Computer-Readable Medium' refers to both machine-storage media and transmission media. Thus, the terms include both storage devices/media and carrier waves/modulated data signals. The terms 'machine-readable medium,' 'computer-readable medium' and 'device-readable medium' mean the same thing and may be used interchangeably in this disclosure.

'Client Device' refers to any machine that interfaces to a communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network. In the subject disclosure, a client device is also referred to as an 'electronic device.'

'Ephemeral Message' refers to a message that is accessible for a time-limited duration. An ephemeral message may be a text, an image, a video and the like. The access time for the ephemeral message may be set by the message sender. Alternatively, the access time may be a default setting or a setting specified by the recipient. Regardless of the setting technique, the message is transitory.

'Signal Medium' refers to any intangible medium that is capable of storing, encoding, or carrying the instructions for execution by a machine and includes digital or analog communications signals or other intangible media to facilitate communication of software or data. The term 'signal medium' shall be taken to include any form of a modulated data signal, carrier wave, and so forth. The term 'modulated data signal' means a signal that has one or more of its characteristics set or changed in such a matter as to encode information in the signal. The terms 'transmission medium' and 'signal medium' mean the same thing and may be used interchangeably in this disclosure.

'Communication Network' refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other types of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long-range protocols, or other data transfer technology.

'Processor' refers to any circuit or virtual circuit (a physical circuit emulated by logic executing on an actual processor) that manipulates data values according to control signals (e.g., 'commands', 'op codes', 'machine code', etc.) and which produces corresponding output signals that are applied to operate a machine. A processor may, for example, be a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC) or any combination thereof. A processor may further be a multi-core processor having two or more independent processors (sometimes referred to as 'cores') that may execute instructions contemporaneously.

'Machine-Storage Medium' refers to a single or multiple storage devices and/or media (e.g., a centralized or distributed database, and/or associated caches and servers) that store executable instructions, routines and/or data. The term shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks The terms 'machine-storage medium,' 'device-storage medium,' 'computer-storage medium' mean the same thing and may be used interchangeably in this disclosure. The terms 'machine-storage media,' 'computer-storage media,' and 'device-storage media' specifically exclude carrier waves, modulated data signals, and other such media, at least some of which are covered under the term 'signal medium.'

'Component' refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A 'hardware component' is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a field-programmable gate array (FPGA) or an application specific integrated circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software), may be driven by cost and time considerations. Accordingly, the phrase 'hardware component'(or 'hardware-implemented component') should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, 'processor-implemented component' refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a 'cloud computing' environment or as a 'software as a service' (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

'Carrier Signal' refers to any intangible medium that is capable of storing, encoding, or carrying instructions for execution by the machine, and includes digital or analog communications signals or other intangible media to facilitate communication of such instructions. Instructions may be transmitted or received over a network using a transmission medium via a network interface device.

'Computer-Readable Medium' refers to both machine-storage media and transmission media. Thus, the terms include both storage devices/media and carrier waves/modulated data signals. The terms 'machine-readable medium,' 'computer-readable medium' and 'device-readable medium' mean the same thing and may be used interchangeably in this disclosure.

'Client Device' refers to any machine that interfaces to a communications network to obtain resources from one or more server systems or other client devices. A client device may be, but is not limited to, a mobile phone, desktop computer, laptop, portable digital assistants (PDAs), smartphones, tablets, ultrabooks, netbooks, laptops, multi-processor systems, microprocessor-based or programmable consumer electronics, game consoles, set-top boxes, or any other communication device that a user may use to access a network.

'Ephemeral Message' refers to a message that is accessible for a time-limited duration. An ephemeral message may be a text, an image, a video and the like. The access time for the ephemeral message may be set by the message sender. Alternatively, the access time may be a default setting or a setting specified by the recipient. Regardless of the setting technique, the message is transitory.

What is claimed is:

1. A method, comprising:
   determining a gaze direction in a field of view of a user using an eyewear device;
   generating an anchor point in the field of view based at least in part on the determined gaze direction;
   identifying a surface corresponding to a ground plane in the field of view, wherein identifying the surface corresponding to the ground plane is based on a surface detection process, and the surface detection process comprises:
   generating a point cloud based on the field of view, the point cloud comprising a set of feature points, each feature point include a set of respective x, y, and z coordinates in a three-dimensional space; and
   performing hit testing on the point cloud to determine a first surface plane in the field of view, the hit testing determining an intersection of at least one feature point corresponding to the first surface plane below a median feature point in the point cloud;
   determining a distance from the identified surface to the anchor point;
   generating augmented reality content based at least in part on the determined distance; and
   rendering the generated augmented reality content in the field of view for display by the eyewear device.

2. The method of claim 1, wherein generating the anchor point comprises:
performing a ray casting operation, based at least in part on the gaze direction, to select a point in the field of view, the point corresponding to the anchor point.

3. The method of claim 2, wherein the ray casting operation comprises:
determining a location of a pupil or iris of the user;
projecting a ray, from the location of the pupil or iris, in a direction toward the field of view, the field of view comprising a set of pixels;
determining at least one pixel from the field of view that intersects the ray; and
selecting the at least one pixel as the anchor point.

4. The method of claim 1, wherein determining the gaze direction is based on a head orientation and a relative position of a pupil or iris of the user using the eyewear device.

5. The method of claim 1, wherein performing hit testing comprises:
generating a three-dimensional line that includes a starting position corresponding to a position of a pupil or iris of the user and extends from the gaze direction to the one feature point corresponding to the first surface plane in the field of view.

6. The method of claim 1, wherein determining the distance from the identified surface to the anchor point comprises:
generating a second anchor point within the identified surface;
determining a first distance between the second anchor point and the anchor point in the field of view, the second anchor point being at a position below relative to the anchor point; and
selecting a particular position along the first distance between the second anchor point and the anchor point.

7. The method of claim 6, wherein rendering the generated augmented reality content in the field of view for display by the eyewear device comprises:
generating a first three-dimensional object; and
rendering the first three-dimensional object at the particular position.

8. The method of claim 7, further comprising:
generating a second three-dimensional object; and
rendering the second three-dimensional object at a second position above or below the first three-dimensional object.

9. The method of claim 8, wherein the first three-dimensional object is different type of object than the second three-dimensional object.

10. The method of claim 8, wherein the first three-dimensional object is a same type of object as the second three-dimensional object.

11. A system comprising:
a processor; and
a memory including instructions that, when executed by the processor, cause the processor to perform operations comprising:
determining a gaze direction in a field of view of a user using an eyewear device;
generating an anchor point in the field of view based at least in part on the determined gaze direction;
identifying a surface corresponding to a ground plane in the field of view, wherein identifying the surface corresponding to the ground plane is based on a surface detection process, and the surface detection process comprises:
generating a point cloud based on the field of view, the point cloud comprising a set of feature points, each feature point include a set of respective x, y, and z coordinates in a three-dimensional space; and
performing hit testing on the point cloud to determine a first surface plane in the field of view, the hit testing determining an intersection of at least one feature point corresponding to the first surface plane below a median feature point in the point cloud;
determining a distance from the identified surface to the anchor point;
generating augmented reality content based at least in part on the determined distance; and
rendering the generated augmented reality content in the field of view for display by the eyewear device.

12. The system of claim 11, wherein generating the anchor point comprises:
performing a ray casting operation, based at least in part on the gaze direction, to select a point in the field of view, the point corresponding to the anchor point.

13. The system of claim 12, wherein the ray casting operation comprises:
determining a location of a pupil or iris of the user;
projecting a ray, from the location of the pupil or iris, in a direction toward the field of view, the field of view comprising a set of pixels;
determining at least one pixel from the field of view that intersects the ray; and
selecting the at least one pixel as the anchor point.

14. The system of claim 11, wherein determining the gaze direction is based on a head orientation and a relative position of a pupil or iris of the user using the eyewear device.

15. The system of claim 11, wherein performing hit testing comprises:
generating a three-dimensional line that includes a starting position corresponding to a position of a pupil or iris of the user and extends from the gaze direction to the one feature point corresponding to the first surface plane in the field of view.

16. The system of claim 11, wherein determining the distance from the identified surface to the anchor point comprises:
generating a second anchor point within the identified surface;
determining a first distance between the second anchor point and the anchor point in the field of view, the second anchor point being at a position below relative to the anchor point; and
selecting a particular position along the first distance between the second anchor point and the anchor point.

17. The system of claim 16, wherein rendering the generated augmented reality content in the field of view for display by the eyewear device comprises:
generating a first three-dimensional object; and
rendering the first three-dimensional object at the particular position.

18. The system of claim 17, further comprising:
generating a second three-dimensional object; and
rendering the second three-dimensional object at a second position above or below the first three-dimensional object.

19. The system of claim 18, wherein the first three-dimensional object is different type of object than the second three-dimensional object.

20. A non-transitory computer-readable medium comprising instructions, which when executed by a computing device, cause the computing device to perform operations comprising:
   determining a gaze direction in a field of view of a user using an eyewear device;
   generating an anchor point in the field of view based at least in part on the determined gaze direction;
   identifying a surface corresponding to a ground plane in the field of view, wherein identifying the surface corresponding to the ground plane is based on a surface detection process, and the surface detection process comprises:
   generating a point cloud based on the field of view, the point cloud comprising a set of feature points, each feature point include a set of respective x, y, and z coordinates in a three-dimensional space; and
   performing hit testing on the point cloud to determine a first surface plane in the field of view, the hit testing determining an intersection of at least one feature point corresponding to the first surface plane below a median feature point in the point cloud;
   determining a distance from the identified surface to the anchor point;
   generating augmented reality content based at least in part on the determined distance; and
   rendering the generated augmented reality content in the field of view for display by the eyewear device.

* * * * *